(12) United States Patent
Rotstein et al.

(10) Patent No.: US 7,625,891 B2
(45) Date of Patent: *Dec. 1, 2009

(54) HETEROCYLIC ANTIVIRAL COMPOUNDS

(75) Inventors: David Mark Rotstein, Sunnyvale, CA (US); Chris Richard Melville, Palo Alto, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/079,746

(22) Filed: Mar. 28, 2008

(65) Prior Publication Data

US 2008/0249087 A1 Oct. 9, 2008

Related U.S. Application Data

(60) Provisional application No. 60/920,694, filed on Mar. 29, 2007.

(51) Int. Cl.
 *C07D 413/14* (2006.01)
 *A61K 31/537* (2006.01)
(52) U.S. Cl. ...................... 514/228.8; 544/71
(58) Field of Classification Search ............... 544/71; 514/228.8
See application file for complete search history.

(56) References Cited

U.S. PATENT DOCUMENTS

| 3,399,192 | A | 8/1968 | Regnier et al. |
|---|---|---|---|
| 6,391,865 | B1 | 5/2002 | Baroudy et al. |
| 6,689,765 | B2 | 2/2004 | Baroudy et al. |
| 2003/0069252 | A1 | 4/2003 | Baroudy et al. |
| 2003/0166928 | A1 | 9/2003 | Schlienger |
| 2005/0176703 | A1 | 8/2005 | Gabriel |

FOREIGN PATENT DOCUMENTS

| EP | 414422 B1 | 4/1994 |
|---|---|---|
| EP | 1236726 B1 | 4/2002 |
| WO | WO 97/11940 A1 | 4/1997 |
| WO | WO 00/66558 A1 | 11/2000 |
| WO | WO 00/66559 A1 | 11/2000 |
| WO | WO 01/57044 A1 | 8/2001 |
| WO | WO 02/092604 A1 | 11/2002 |
| WO | WO 03/057698 A2 | 7/2003 |
| WO | WO 03/057698 A3 | 7/2003 |
| WO | WO 2007/085567 A2 | 8/2007 |
| WO | WO 2007/085567 A3 | 8/2007 |

OTHER PUBLICATIONS

Caroon, J., et al.; "Synthesis and Antihypertensive Activity of a Series of 8-Substituted 1-Oxa-3,8-diazaspiro [4.5]decan-2-ones[1]" *J. Med. Chem.* (1981) vol. 24, pp. 1320-1328.

Clark, R., et al.; "Antihypertensive 9-Substituted 1-Oxa-4,9-diazaspiro[5.5]undecan-3-ones[1]" *J. Med. Chem.* (1983) vol. 26, pp. 855-861.

Kazmierski, W., et al.; "Recent Progress in Discovery of Small-Molecule CCR5 Chemokine Receptor Ligands as HIV-1 Inhibitors," *Bioorganic & Medicinal Chemistry* (2003) vol. 11, pp. 2663-2676.

Palani, A., et al.; "An Orally Bioavailable Human CCR5 Antagonist for the Treatment of HIV Infection," *J. Medicinal Chemistry* (2001), vol. 44:21, pp. 3339-3342.

Smith, P.W., et al., "New Spiropiperidines as Potent and Selective Non-Peptide Tachykinin $NK_2$," *J. Med. Chem.* (1995) vol. 38, pp. 3772-3779.

Tagat, J., et al.; "Piperazine-Based CCR5 Antagonists as HIV-1 Inhibitors," *J. Med. Chem.* (2001) vol. 44, pp. 3343-3346.

*Primary Examiner*—Kahsay T Habte
(74) *Attorney, Agent, or Firm*—Brian L. Buckwalter

(57) ABSTRACT

This invention relates to piperidine derivatives of formula I wherein $R^1$, $R^2$, $R^3$ and $R^4$ are as defined herein useful in the treatment of a variety of disorders, including those in which the modulation of CCR5 receptors is implicated. Disorders that may be treated or prevented by the present derivatives include HIV and genetically related retroviral infections (and the resulting acquired immune deficiency syndrome, AIDS), rheumatoid arthritis, solid organ transplant reject (graft vs. host disease), asthma and COPD.

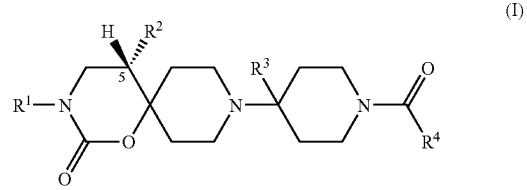

(I)

20 Claims, No Drawings

HETEROCYLIC ANTIVIRAL COMPOUNDS

CROSS REFERENCE TO PRIOR APPLICATIONS

This application is claims benefit of U.S. Provisional Application No. 60/920,694, filed Mar. 29, 2007, which is hereby incorporated by reference in its entirety.

FIELD OF THE INVENTION

This invention relates to piperidine derivatives useful in the treatment of a variety of disorders in which modulation of the CCR5 receptor ligand binding is beneficial. More particularly, to 1-oxa-3,9-diaza-spiro[5.5]undecan-2-one compounds, to compositions containing said compounds and to uses of such derivatives. Disorders that may be treated or prevented by the present compounds include HIV-1 and genetically related retroviral infections (and the resulting acquired immune deficiency syndrome, AIDS), arthritis, rheumatoid arthritis, asthma, chronic obstructive pulmonary disease (COPD) and rejection of transplanted organs.

BACKGROUND OF THE INVENTION

Compounds of the present invention modulate the activity of the chemokine CCR5 receptors. The CCR5 receptor is a member of a subset of a large family chemokine receptors characterized structurally by two adjacent cysteine residues. Human chemokines include approximately 50 small proteins of 50-120 amino acids that are structurally homologous. (M. Baggiolini et al., *Ann. Rev. Immunol.* 1997 15:675-705) The chemokines are pro-inflammatory peptides (reviewed in Luster, *New Eng. J. Med.* 1998 338:436-445 and Rollins, *Blood* 1997 90:909-928). The name "chemokine" is a contraction of "chemotactic cytokines". The chemokines are a family of leukocyte chemotactic proteins that are released by a wide variety of cells such as macrophages, monocytes, eosinophils, neutrophiles, fibroblasts, vascular endothelial cells, smooth muscle cells, and mast cells, at inflammatory sites and attract leukocytes to various tissues, which is an essential response to inflammation and infection. Chemokines can be grouped into two subfamilies, based on whether the two amino terminal cysteine residues are immediately adjacent (CC family) or separated by one amino acid (CXC family). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES (CCL5), MIP-1α (CCL3, macrophage inflammatory protein), MIP-1β (CCL4), the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. Naturally occurring chemokines which can stimulate the CCR5 receptor include MIP-1α, MIP-1β and RANTES.

Accordingly, drugs which inhibit the binding of chemokines such as MIP-1α, MIP-1β and RANTES to these receptors, e.g., chemokine receptor antagonists, may be useful as pharmaceutical agents which inhibit the action of chemokines such as MIP-1α, MIP-1β and RANTES on the target cells. The identification of compounds that modulate the function of CCR5 represents an excellent drug design approach to the development of pharmacological agents for the treatment of inflammatory conditions and diseases associated with CCR5 receptor.

The pharmacokinetic challenges associated with large molecules, proteins and peptides resulted in the establishment of programs to identify low molecular weight antagonists of CCR5. The efforts to identify chemokine modulators have been reviewed. (W. Kazmierski et al. *Biorg Med. Chem.* 2003 11:2663-76; L. Agrawal and G. Alkhatib, *Expert Opin. Ther. Targets* 2001 5(3):303-326; *Chemokine CCR5 antagonists incorporating 4-aminopiperidine scaffold, Expert Opin. Ther. Patents* 2003 13(9):1469-1473; M. A. Cascieri and M. S. Springer, *Curr. Opin. Chem. Biol.* 2000 4:420-426, and references cited therein)

Low Molecular-Weight CCR5 Antagonists

Takeda's identified TAK-779 as a potential CCR5 antagonist. (M. Shiraishi et al., *J. Med. Chem.* 2000 43(10):2049-2063; M. Babba et al. *Proc. Nat. Acad. Sci. USA* 1999 96:5698-5703) and TAK-220 (C. Tremblay et al. *Antimicrob. Agents Chemother.* 2005 49(8):3483-3485).

WO0039125 (D. R. Armour et al.) and WO0190106 (M. Perros et al.) disclose heterocyclic compounds that are potent and selective CCR5 antagonists. Pfizer's UK427,857 (MVC) has been approved by the FDA for treating HIV-1. (P. Dorr et al., *Antimicrob. Agents Chemother.* 2005 49(11):4721-4732; A. Wood and D. Armour, *Prog. Med. Chem.* 2005 43:239-271; C. Watson et al., *Mol. Pharm.* 2005 67(4):1268-1282; M. J. Macartney et al., 43$^{rd}$ *Intersci. Conf. Antimicrob. Agents Chemother.* Sep. 14-17, 2003, Abstract H-875)

Schering has advanced Sch-351125 (SCH-C) into Phase I/II clinical studies and reported the advance of a more potent follow-up compound, Sch-417690 (SCH-D) into Phase I studies. (S. W. McCrombie et al., WO00066559; B. M. Baroudy et al. WO00066558; A. Palani et al., *J. Med. Chem.* 2001 44(21):3339-3342; J. R. Tagat et al., *J. Med. Chem.* 2001 44(21):3343-3346; J. A. Esté, *Cur. Opin. Invest. Drugs* 2002 3(3):379-383; J. M. Struzki et al. *Proc. Nat. Acad. Sci. USA* 2001 98:12718-12723).

Merck has disclosed the preparation of (2S)-2-(3-chlorophenyl)-1-N-(methyl)-N-(phenylsulfonyl)amino]-4-[spiro (2,3-dihydrobenzothiophene-3,4'-piperidin-1'-yl)butane S-oxide (1) and related derivatives, trisubstituted pyrrolidines 2 and substituted piperidines 3 with good affinity for the CCR5 receptor and potent-HIV-1 activity. (P. E. Finke et al., *Bioorg. Med. Chem. Lett.,* 2001 11:265-270; P. E. Finke et al., *Bioorg. Med. Chem. Lett.,* 2001 11:2469-2475; P. E. Finke et al., *Bioorg. Med. Chem. Lett.,* 2001 11:2475-2479; J. J. Hale et al., *Bioorg. Med. Chem. Lett.,* 2001 11:2741-22745; D. Kim et al., *Bioorg. Med. Chem. Lett.,* 2001 11:3099-3102) C. L. Lynch et al. *Org. Lett.* 2003 5:2473-2475; R. S. Veazey et al. *J. Exp. Med.* 2003 198:1551-1562.

ONO-4128, E-913, AK-602 was identified in a program initiated at Kumamoto University (K. Maeda et al. *J. Biol. Chem.* 2001 276:35194-35200; H. Nakata et al. *J. Virol.* 2005 79(4):2087-2096)

In WO00/166525; WO00/187839; WO02/076948; WO02/076948; WO02/079156, WO2002070749, WO2003080574, WO2003042178, WO2004056773, WO2004018425 Astra Zeneca disclose 4-amino piperidine compounds which are CCR5 antagonists.

EP1236726 (H. Habashita et al.) discloses triazaspiro[5.5] undecane derivatives exemplified by AK602 which modulate the cytokine receptors. The compounds fall outside the scope of the current invention. (H. Nakata et al. Poster 546a, 11$^{th}$ Conference on Retroviruses and Opportunistic Infections, San Francisco, Calif., Feb. 8-11, 2004; other analogs have also been disclosed, see, e.g. K. Maeda et al., *J. Biol. Chem.* 2001 276(37): 35194-35200)

The aforementioned compounds fall outside the scope of the present invention.

In U.S. Patent Publication 20050176703 published Aug. 11, 2005 S. D. Gabriel et al. disclosed 1-oxa-3,8-diaza-spiro[4.5]decan-2-one and 1-oxa-3,9-diaza-spiro[5.5]undecan-2-one derivatives which are CCR5 receptor antagonists.

SUMMARY OF THE INVENTION

The present invention relates to compounds according to formula I and pharmaceutical compositions for treating diseases mediated by the CCR5 receptor binding or activation said compound having a structure according to formula I admixed with at least one carrier, diluent or excipient wherein:

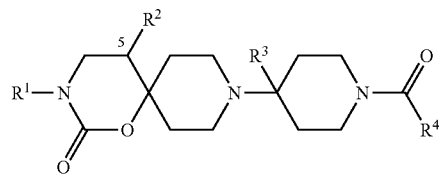
(I)

$R^1$ is: (a) $C_{3-6}$ cycloalkyl, wherein said cycloalkyl is optionally substituted with one to three groups independently selected from the group consisting of hydroxy, $C_{1-3}$ alkyl, oxo, halogen, $C_{1-6}$ alkoxy-oximino and $C_{1-6}$ alkoxy-$C_{1-6}$ alkoxy;

(b) $C_{3-6}$ cycloalkyl-$C_{1-3}$ alkyl wherein said cycloalkyl is optionally substituted with one to three groups independently selected from the group consisting of hydroxy, $C_{1-3}$ alkyl, oxo, halogen, $C_{1-6}$ alkoxy-oximino and $C_{1-6}$ alkoxy-$C_{1-6}$ alkoxy with the proviso that said $C_{3-6}$ cycloalkyl-$C_{1-3}$ alkyl is not 4,4-difluorocyclohexyl-methyl or 1-hydroxyl-cyclohexyl-methyl (c)

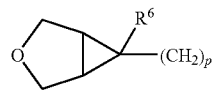

wherein $R^6$ is hydrogen or halogen;

(d)

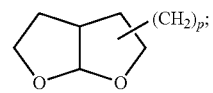

(e)

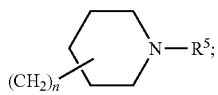

(f)

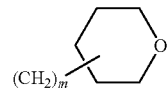

wherein m is 0 or 2;

(g) heteroaryl, hetoroaryl $C_{1-3}$ alkyl, phenyl $C_{1-3}$ alkyl wherein said heteroaryl is pyridine, pyrimidine, pyrazine or pyridazine and said heteroaryl or said phenyl is independently substituted with 1 to 3 substituents independently selected from $C_{1-6}$ alkyl, halogen, $C_{1-6}$ alkoxy, cyano or nitro;

(h) $C_{1-6}$ haloalkyl;

(i)

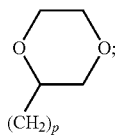

(j)

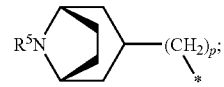

(k)

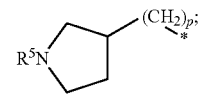

(l)

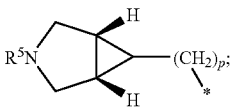

$R^2$ is $C_{1-6}$ alkyl;

$R^3$ is hydrogen or $C_{1-3}$ alkyl;

$R^4$ is selected from the group consisting of (a)-(i) and (j):
(a) 4,6-dimethyl-pyrimidin-5-yl;
(b) 4,6-dimethyl-2-trifluoromethyl-pyrimidin-5-yl;
(c) 2,4-dimethyl-pyridin-3-yl;
(d) 2,4-dimethyl-1-oxy-pyridin-3-yl;
(e) 6-cyano-2,4-dimethyl-pyridin-3-yl;
(f) 2,4-dimethyl-6-oxo-6H-pyran-3-yl
(g) 2,4-dimethyl-6-oxo-1,6-dihydro-pyridin-3-yl;
(h) 1,2,4-trimethyl-6-oxo-1,6-dihydro-pyridin-3-yl;
(i) 3,5-dimethyl-1-oxy-1H-pyrazol-4-yl; and,
(j) 5-cyano-2,4-dimethyl-1H-pyrrol-3-yl; or,
(k) 3-methyl-5-trifluoromethyl-isoxazol-4-yl
(l) 3,5-dimethyl-1-hydroxy-pyrazol-4-yl;

$R^5$ is $C_{1-6}$ acyl, $C_{1-6}$ alkoxycarbonyl, $C_{1-6}$ alkyl $SO_2$, $C_{1-6}$ haloalkyl, $C_{3-6}$ cycloalkyl, oxetanyl, tetrahydrofuranyl or tetrahydropyranyl;

p is 1 or 3 and n is 0 to 3; or a pharmaceutically acceptable acid addition salt thereof.

The present invention further relates to a method for treating an HIV-1 infection by administering a compound of formula I, either alone or in combination with one or more compounds which inhibit replication of HIV-1. Compounds which inhibit HIV-1 replication include reverse transcriptase inhibitors, protease inhibitors, and viral fusion inhibitors.

The present invention further relates to a method for treating rheumatoid arthritis utilizing a compound of formula I, either alone or in combination with other anti-inflammatory agents useful for alleviation of arthritis.

The present invention also relates to a method for treating inflammatory diseases of the lung and airways including asthma and chronic obstructive pulmonary disease (COPD).

The present invention further relates a method for treating transplant rejection utilizing a compound of formula I, either alone or in combination with other anti-rejection drugs or immune system modulators.

The combination therapy utilizing the present compounds can be accomplished with both low-molecular weight compounds and with antibodies.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

In an embodiment of the present invention there is provided a compound according to formula I wherein $R^1$, $R^2$, $R^3$, $R^4$, $R^5$, $R^6$, m, n and p are as defined herein above providing that $R^1$ is not 4,4-difluorocyclohexyl-methyl or 1-hydroxyl-cyclohexyl-methyl. Substituent definitions in this and the following embodiments which are not specifically limited in the description of the embodiment retain the broadest scope defined in the Summary of the Invention. Furthermore all the embodiments include pharmaceutically acceptable salts of the compounds of formula I.

In another embodiment of the present invention there is provided a compound according to formula I wherein $R^5$ is (a) to (g) or (i); $R^4$ is (a) to (i) or (j) and n is 1 to 3; or a pharmaceutically acceptable acid addition salt thereof.

In second embodiment of the present invention there is provided a compound according to formula I wherein $R^1$ is 4-alkoxy-cyclohexylmethyl, or 4-hydroxy-cyclohexylmethyl, $R^3$ is methyl and $R^4$ is (a), (c) or (e) or a pharmaceutically acceptable acid addition salt thereof.

In another embodiment of the present invention there is provided a compound according to formula I wherein $R^1$ is 4-alkoxy-cyclohexylmethyl, $R^3$ is methyl and $R^4$ is (a), (c) or (e) or a pharmaceutically acceptable acid addition salt thereof.

In still another embodiment of the present invention there is provided a compound according to formula I wherein $R^1$ is 4-methoxy-cyclohexylmethyl or 4-ethoxy-cyclohexylmethyl, $R^3$ is methyl and $R^4$ is (a), (c) or (e) or a pharmaceutically acceptable acid addition salt thereof.

In a third embodiment of the present invention there is provided a compound according to formula I wherein $R^1$ is 4-alkoxy-cyclohexylmethyl, or 4-hydroxy-cyclohexylmethyl, $R^3$ is methyl, $R^4$ is (a), (c) or (e) and the C-5 configuration is S or a pharmaceutically acceptable acid addition salt thereof.

In another embodiment of the present invention there is provided a compound according to formula I wherein $R^1$ is 4-alkoxy-cyclohexylmethyl, $R^3$ is methyl, $R^4$ is (a), (c) or (e) and the C-5 configuration is S or a pharmaceutically acceptable acid addition salt thereof.

In a fourth embodiment of the present invention there is provided a compound according to formula I wherein $R^1$ is (e), (j), (k) or (l), $R^3$ is methyl and $R^4$ is (a), (c) or (e) or a pharmaceutically acceptable acid addition salt thereof.

In another embodiment of the present invention there is provided a compound according to formula I wherein $R^1$ is (e), n is 1, $R^3$ is methyl and $R^4$ is (a), (c) or (e) or a pharmaceutically acceptable acid addition salt thereof.

In yet another embodiment of the present invention there is provided a compound according to formula I wherein $R^1$ is (O), (k) or (l), p is 1, $R^3$ is methyl and $R^4$ is (a), (c) or (e) or a pharmaceutically acceptable acid addition salt thereof.

In a fifth embodiment of the present invention there is provided a compound according to formula I wherein $R^1$ is (e), (j), (k) or (l), $R^3$ is methyl, $R^4$ is (a), (c) or (e) and $R^5$ is $C_{1-6}$ alkoxycarbonyl or 2,2-difluoroethyl or a pharmaceutically acceptable acid addition salt thereof.

In still another embodiment of the present invention there is provided a compound according to formula I wherein $R^1$ is (e), $R^3$ is methyl, $R^4$ is (a), (c) or (e) and $R^5$ is $C_{1-6}$ alkoxycarbonyl or 2,2-difluoroethyl or a pharmaceutically acceptable acid addition salt thereof. In still yet another embodiment of the present invention there is provided a compound according to formula I wherein $R^1$ is (e), $R^3$ is methyl, $R^4$ is (a), (c) or (e) and $R^5$ is $C_{1-6}$ alkylsulfonyl or a pharmaceutically acceptable acid addition salt thereof.

In yet another embodiment of the present invention there is provided a compound according to formula I wherein $R^1$ is (j), (k) or (l), $R^3$ is methyl, $R^4$ is (a), (c) or (e) and $R^5$ is $C_{1-6}$ alkoxycarbonyl or $C_{1-6}$ fluoroalkyl or a pharmaceutically acceptable acid addition salt thereof. In still yet another embodiment of the present invention there is provided a compound according to formula I wherein $R^1$ is (j), (k) or (l), $R^3$ is methyl, $R^4$ is (a), (c) or (e) and $R^5$ is $C_{1-6}$ alkylsulfonyl or a pharmaceutically acceptable acid addition salt thereof.

In a sixth embodiment of the present invention there is provided a compound according to formula I wherein $R^1$ is (e), (j), (k) or (l), $R^3$ is methyl, $R^4$ is (a), (c) or (e), $R^5$ is $C_{1-6}$ alkoxycarbonyl or 2,2-difluoroethyl and the C-5 configuration is S or a pharmaceutically acceptable acid addition salt thereof.

In still another embodiment of the present invention there is provided a compound according to formula I wherein $R^1$ is (e), $R^3$ is methyl, $R^4$ is (a), (c) or (e), $R^5$ is $C_{1-6}$ alkoxycarbonyl or 2,2-difluoroethyl and the C-5 configuration is S or a pharmaceutically acceptable acid addition salt thereof.

In a seventh embodiment of the present invention there is provided a compound according to formula wherein $R^1$ is (c), (d) or (i), $R^3$ is methyl, $R^4$ is (a), (c) or (e) and the C-5 configuration is S or a pharmaceutically acceptable acid addition salt thereof.

In another embodiment of the present invention there is provided a compound according to formula I wherein $R^1$ is (c), (d) or (i), p is 1, $R^3$ is methyl, $R^4$ is (a), (c) or (e) and the C-5 configuration is S or a pharmaceutically acceptable acid addition salt thereof.

In still another embodiment of the present invention there is provided a compound according to formula I wherein $R^1$ is (c) or (d), p is 1, $R^3$ is methyl, $R^4$ is (a), (c) or (e) and the C-5 configuration is S or a pharmaceutically acceptable acid addition salt thereof.

In yet another embodiment of the present invention there is provided a compound according to formula I wherein $R^1$ is (c), p is 1, $R^3$ is methyl, $R^4$ is (a), (c) or (e) and the C-5 configuration is S or a pharmaceutically acceptable acid addition salt thereof.

In another embodiment of the present invention there is provided a compound according to formula I wherein $R^1$ is (d), p is 1, $R^3$ is methyl, $R^4$ is (a), (c) or (e) and the C-5 configuration is S or a pharmaceutically acceptable acid addition salt thereof.

In an eighth embodiment of the present invention there is provided a compound according to formula wherein $R^1$ is (g), $R^3$ is methyl, $R^4$ is (a), (c) or (e) and the C-5 configuration is S or a pharmaceutically acceptable acid addition salt thereof.

In another embodiment of the present invention there is provided a compound according to formula I wherein $R^1$ is pyridinyl pyrimidinyl or pyrimidinylmethyl, $R^3$ is methyl, $R^4$ is (a), (c) or (e) and the C-5 configuration is S or a pharmaceutically acceptable acid addition salt thereof.

In still another embodiment of the present invention $R^1$ is (h), $R^3$ is methyl, $R^4$ is (a), (c) or (e), and the C-5 configuration is S.

In another embodiment of the present invention there is provided a compound selected from compounds I-1 to I-10 in TABLE 1, compounds II-1 to II-13 in TABLE II, compounds III-1 to III-26 in TABLE III or compounds IV-1 to IV-12 in TABLE IV.

In still another embodiment of the present invention there is provided a compound selected from compounds I-1 to I-9 in TABLE 1, compounds II-1 to II-8 in TABLE II, compounds III-1 to III-12 in TABLE III or compounds IV-1 to IV-12 in TABLE IV.

In tenth of the present invention there is provided a method of treating or preventing an human immunodeficiency virus (HIV) infection, or treating AIDS or ARC, in a patient in need thereof which comprises administering to the patient in need thereof a therapeutically effective amount of a compound according to formula I wherein $R^1$, $R^2$, $R^3$, $R^4$, $R^5$, $R^6$, m, n and p are as defined herein above providing that $R^1$ is not 4,4-difluorocyclohexyl-methyl or 1-hydroxyl-cyclohexyl-methyl.

In an eleventh embodiment of the present invention there is provided a method of treating or preventing an human immunodeficiency virus (HIV) infection, or treating AIDS or ARC, in a patient in need thereof which comprises administering to the patient in need thereof a therapeutically effective amount of a compound according to formula I wherein $R^1$ is cis- or trans-4-alkoxy-cyclohexylmethyl or cis- or trans-4-hydroxy-cyclohexylmethyl, $R^3$ is methyl, $R^4$ is (a), (c) or (e), the C-5 configuration is S and $R^2$ is as defined herein above In a twelfth embodiment of the present invention there is provided a method of treating or preventing an human immunodeficiency virus (HIV) infection, or treating AIDS or ARC, in a patient in need thereof which comprises administering to the patient in need thereof a therapeutically effective amount of a compound according to formula I wherein $R^1$ is (e), (j), (k) or (l), $R^3$ is methyl, $R^4$ is (a), (c) or (e), $R^5$ is $C_{1-6}$ alkoxycarbonyl or 2,2,-difluoroethyl, n is 1, the C-5 configuration is S and $R^2$ is as defined herein above In a another embodiment of the present invention there is provided a method of treating or preventing an human immunodeficiency virus (HIV) infection, or treating AIDS or ARC, in a patient in need thereof which comprises administering to the patient in need thereof a therapeutically effective amount of a compound according to formula I wherein $R^1$ is (e), $R^3$ is methyl, $R^4$ is (a), (c) or (e), $R^5$ is methoxycarbonyl, n is 1, the C-5 configuration is S and $R^2$ is as defined herein above In a thirteenth embodiment of the present invention there is provided a method of treating or preventing an human immunodeficiency virus (HIV) infection, or treating AIDS or ARC, in a patient in need thereof which comprises administering to the patient in need thereof a therapeutically effective amount of a compound according to formula I wherein $R^1$ is (c), (d) or (i), p is 1 $R^3$ is methyl, $R^4$ is (a), (c) or (e), the C-5 configuration is S and $R^2$ is as defined herein above.

In a fourteenth embodiment of the present invention there is provided a method of treating or preventing an human immunodeficiency virus (HIV) infection, or treating AIDS or ARC, in a patient in need thereof which comprises co-administering a therapeutically effective amount of one or more inhibitors selected from the group consisting of HIV-1 nucleoside reverse transcriptase inhibitors, non-nucleoside reverse transcriptase inhibitors, HIV-1 protease inhibitors and HIV-1 viral fusion inhibitors and a compound of claim 1 wherein $R^1$, $R^2$, $R^3$, $R^4$, $R^5$, $R^6$, m, n and p are as defined herein above providing that $R^1$ is not 4,4-difluorocyclohexyl-methyl or 1-hydroxyl-cyclohexyl-methyl.

In a fifteenth embodiment of the present invention there is provided a method for treating rheumatoid arthritis comprising administering to a patient in need thereof a therapeutically effective amount of a compound according to claim formula I wherein $R^1$, $R^2$, $R^3$, $R^4$, $R^5$, $R^6$, m, n and p are as defined herein above providing that $R^1$ is not 4,4-difluorocyclohexyl-methyl or 1-hydroxyl-cyclohexyl-methyl.

In a sixteenth embodiment of the present invention there is provided a method for treating rheumatoid arthritis comprising co-administering to a patient in need thereof one or more anti-inflammatory or analgesic compounds and a compound according to claim formula I wherein $R^1$, $R^2$, $R^3$, $R^4$, $R^5$, $R^6$, m, n and p are as defined herein above providing that $R^1$ is not 4,4-difluorocyclohexyl-methyl or 1-hydroxyl-cyclohexyl-methyl.

In a seventeenth embodiment of the present invention there is provided a method for treating asthma or congestive obstructive pulmonary disease (COPD) comprising administering to a patient in need thereof a therapeutic amount of a compound according to claim formula I wherein $R^1$, $R^2$, $R^3$, $R^4$, $R^5$, $R^6$, m, n and p are as defined herein above providing that $R^1$ is not 4,4-difluorocyclohexyl-methyl or 1-hydroxyl-cyclohexyl-methyl.

In an eighteenth embodiment of the present invention there is provided a method for treating solid organ transplant rejection comprising administering to a patient in need thereof a therapeutically effective amount of a compound according to claim formula I wherein $R^1, R^2, R^3, R^4, R^5, R^6$, m, n and p are as defined herein above providing that $R^1$ is not 4,4-difluoro-cyclohexyl-methyl or 1-hydroxyl-cyclohexyl-methyl.

In a nineteenth embodiment of the present invention there is provided a method for treating solid organ transplant rejection comprising co-administering to a patient in need thereof one or more anti-rejection drugs or immunomodulators and a compound according to formula I wherein $R^1, R^2, R^3, R^4, R^5, R^6$, m, n and p are as defined herein above providing that $R^1$ is not 4,4-difluorocyclohexyl-methyl or 1-hydroxyl-cyclohexyl-methyl.

In a twentieth embodiment of the present invention there is provided a pharmaceutical composition comprising a compound according to formula I wherein to a patient in need thereof and at least one pharmaceutically acceptable carrier, diluent or excipient.

Methods for Treating HIV-1 Infections

HIV-1 infects cells of the monocyte-macrophage lineage and helper T-cell lymphocytes by exploiting a high affinity interaction of the viral enveloped glycoprotein (Env) with the CD-4 antigen. The CD-4 antigen was found to be a necessary, but not sufficient requirement for cell entry and at least one other surface protein was required to infect the cells (E. A. Berger et al., *Ann. Rev. Immunol.* 1999 17:657-700). Two chemokine receptors, either the CCR5 or the CXCR4 receptor were subsequently found to be co-receptors along with CD4 which are required for infection of cells by the human immunodeficiency virus (HIV). The central role of CCR5 in the pathogenesis of HIV was inferred by epidemiological identification of powerful disease modifying effects of the naturally occurring null allele CCR5 Δ32. The Δ32 mutation has a 32-base pair deletion in the CCR5 gene resulting in a truncated protein designated Δ32. Relative to the general population, Δ32/Δ32 homozygotes are significantly common in exposed/uninfected individuals suggesting the role of CCR5 in HIV cell entry (R. Liu et al., *Cell* 1996 86(3):367-377; M. Samson et al., *Nature* 1996 382(6593):722-725). The CD4 binding site on the gp120 of HIV appears to interact with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. Accordingly, an agent which could block chemokine receptors in humans who possess normal chemokine receptors should prevent infection in healthy individuals and slow or halt viral progression in infected patients.

RANTES and an analog chemically modified on the N-terminus, aminooxypentane RANTES, were found to block HIV entry into the cells. (G. Simmons et al., *Science* 1997 276:276-279). Other compounds have been demonstrated to inhibit the replication of HIV, including soluble CD4 protein and synthetic derivatives (Smith, et al., *Science* 1987 238: 1704-1707), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

A-M. Vandamme et al. (*Antiviral Chemistry & Chemotherapy*, 1998 9:187-203) disclose current HAART clinical treatments of HIV-1 infections in man including at least triple drug combinations. Highly active anti-retroviral therapy (HAART) has traditionally consisted of combination therapy with nucleoside reverse transcriptase inhibitors (NRTI), non-nucleoside reverse transcriptase inhibitors (NNRTI) and protease inhibitors (PI). These compounds inhibit biochemical processes required for viral replication. While HAART has dramatically altered the prognosis for HIV infected persons, there remain many drawbacks to the current therapy including highly complex dosing regimes and side effects which can be very severe (A. Carr and D. A. Cooper, *Lancet* 2000 356(9239):1423-1430). Moreover, these multidrug therapies do not eliminate HIV-1 and long-term treatment usually results in multidrug resistance, thus limiting their utility in long-term therapy. Development of new therapeutics which can be used in combination with NRTIs, NNRTIs, PIs and viral fusion inhibitors to provide better HIV-1 treatment remains a priority.

Typical suitable NRTIs include zidovudine (AZT; RETROVIR®); didanosine (ddI; VIDEX®); zalcitabine (ddC; HUVID®); stavudine (d4T; ZERIT®); lamivudine (3TC; EPIVIR); abacavir (ZIAGEN®); adefovir dipivoxil [bis (POM)-PMEA; PREVON®]; lobucavir (BMS-180194), a nucleoside reverse transcriptase inhibitor disclosed in EP-0358154 and EP-0736533; BCH-10652, a reverse transcriptase inhibitor (in the form of a racemic mixture of BCH-10618 and BCH-10619) under development by Biochem Pharma; emitricitabine [(−)-FTC] in development by Triangle Pharmaceuticals; β-L-FD4 (also called β-L-D4C and named β-L-2',3'-dicleoxy-5-fluoro-cytidene) licensed Vion Pharmaceuticals; DAPD, the purine nucleoside, (−)-β-D-2,6-diamino-purine dioxolane disclosed in EP-0656778 and licensed to Triangle Pharmaceuticals; and lodenosine (FddA), 9-(2,3-dideoxy-2-fluoro-β-D-threo-pentofuranosyl) adenine, an acid stable purine-based reverse transcriptase inhibitor under development by U.S. Bioscience Inc.

Typical suitable NNRTIs include nevirapine (BI-RG-587; VIRAMUNE®); delaviradine (BHAP, U-90152; RESCRIPTOR®); efavirenz (DMP-266; SUSTUVA); PNU-142721, a furopyridine-thio-pyrimidine under development by Pfizer; AG-1549 (formerly Shionogi # S-11153); 5-(3,5-dichlorophenyl)-thio-4-isopropyl-1-(4-pyridyl)methyl-1H-imidazol-2-ylmethyl carbonate disclosed in WO 96/10019; MKC442 (1-(ethoxy-methyl)-5-(1-methylethyl)-6-(phenyl-methyl)-(2,4(1H, 3H)-pyrimidinedione); and (+)-calanolide A (NSC-675451) and B, coumarin derivatives disclosed in U.S. Pat. No. 5,489,697.

Typical suitable PIs include saquinavir (Ro 31-8959; INVIRASE®; FORTOVASE®); ritonavir (ABT-538; NORVIR®); indinavir (MK-639; CRIXVAN®); nelfnavir (AG-1343; VIRACEPT®); amprenavir (141W94; AGENERASE®); lasinavir (BMS-234475); DMP450, a cyclic urea under development by Triangle Pharmaceuticals; BMS-2322623, an azapeptide under development by Bristol-Myers Squibb as a 2nd-generation HIV-1 PI; ABT-378 under development by Abbott; and AG-1549 an imidazole carbamate under development by Agouron Pharmaceuticals, Inc.

Other antiviral agents include hydroxyurea, ribavirin, IL-2, IL-12, pentafuside. Hydroxyurea (Droxia), a ribonucleoside triphosphate reductase inhibitor shown to have a synergistic effect on the activity of didanosine and has been studied with stavudine. IL-2 (aldesleukin; PROLEUKIN®) is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314. Pentafuside (FUZEON®) a 36-amino acid synthetic peptide that inhibits fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred. Ribavirin, 1-β-D-ribofuranosyl-1H-1,2,4-triazole-3-carboxamide.

In addition to the potential for CCR5 modulators in the management of HIV infections, the CCR5 receptor is an important regulator of immune function and compounds of the present invention may prove valuable in the treatment of disorders of the immune system. Treatment of solid organ transplant rejection, graft v. host disease, arthritis, rheumatoid arthritis, inflammatory bowel disease, atopic dermatitis, psoriasis, asthma, allergies or multiple sclerosis by administering to a human in need of such treatment an effective amount of a CCR5 antagonist compound of the present invention is also possible.

Methods for Treating Rheumatoid Arthritis

Modulators of the CCR5 receptor may be useful in the treatment of various inflammatory conditions. Rheumatoid arthritis is characterized by infiltration of memory T lymphocytes and monocytes into inflamed joints. As leukocyte chemotactic factors, chemokines play an indispensable role in the attraction of macrophages to various tissues of the body, a process which is essential for both inflammation and the body's response to infection. Because chemokines and their receptors regulate trafficking and activation of leukocytes which contribute to the pathophysiology of inflammatory and infectious diseases, agents which modulate CCR5 activity, preferably antagonizing interactions of chemokines and their receptors, are useful in the therapeutic treatment of such inflammatory diseases.

Elevated levels of CC chemokines, especially CCL2, CCL3 and CCL5, have been found in the joints of patients with rheumatoid arthritis and have been correlated with the recruitment on monocytes and T cells into synovial tissues (I. F. Charo and R. M. Ransohoff, *New Eng. J. Med.* 2006 354: 610-621). T-cells recovered from synovial fluid of rheumatoid arthritis have been shown to express CCR5 and CXCR3. P. Gao et al., *J. Leukocyte Biol.* 2003 73:273-280) Met-RANTES is an amino-terminal modified RANTES derivative which blocks RANTES binding to the CCR1 and CCR5 receptors with nanomolar potency. (A. E. Proudfoot et al., *J. Biol. Chem.* 1996 271:2599-2603). The severity of arthritis in rat adjuvant-induced arthritis was reduced by the administration of Met-RANTES. In addition, the levels of pro-inflammatory cytokines TNF-α and IL-1β. (S. Shahrara et al. *Arthr. & Rheum.* 2005 52:1907-1919) Met-RANTES has been shown to ameliorate the development of inflammation in an art recognized rodent model of inflammation, the collagen induced arthritis. (C. Plater-Zyberk et al. *Immunol. Lett.* 1997 57:117-120)

TAK-779 has also been shown to reduce both the incidence and severity of arthritis in the collagen-induced arthritis model. The antagonist inhibited the infiltration of inflammatory CCR5+ T-cells into the joint. (Y.-F. Yang et al., *Eur. J. Immunol.* 2002 32:2124-2132). Another CCR5 antagonist, SCH-X, was shown to reduce the incidence and severity of collagen-induced arthritis in rhesus monkeys. (M. P. M. Vierboom et al., *Arthr. & Rheum.* 2005 52(20):627-636).

In some anti-inflammatory conditions compounds of the present invention may be administered in combination with other anti-inflammatory drugs which may have a alternative mode of action. Compounds which may be combined with CCR5 antagonists include, but are not limited to:

Methods for Treating Rheumatoid Arthritis

Modulators of the CCR5 receptor may be useful in the treatment of various inflammatory conditions. Rheumatoid arthritis is characterized by infiltration of memory T lymphocytes and monocytes into inflamed joints. As leukocyte chemotactic factors, chemokines play an indispensable role in the attraction of macrophages to various tissues of the body, a process which is essential for both inflammation and the body's response to infection. Because chemokines and their receptors regulate trafficking and activation of leukocytes which contribute to the pathophysiology of inflammatory and infectious diseases, agents which modulate CCR5 activity, preferably antagonizing interactions of chemokines and their receptors, are useful in the therapeutic treatment of such inflammatory diseases.

Elevated levels of CC chemokines, especially CCL2, CCL3 and CCL5, have been found in the joints of patients with rheumatoid arthritis and have been correlated with the recruitment on monocytes and T cells into synovial tissues (I. F. Charo and R. M. Ransohoff, *New Eng. J. Med.* 2006 354: 610-621). T-cells recovered from synovial fluid of rheumatoid arthritis have been shown to express CCR5 and CXCR3. P. Gao et al., *J. Leukocyte Biol.* 2003 73:273-280) Met-RANTES is an amino-terminal modified RANTES derivative which blocks RANTES binding to the CCR1 and CCR5 receptors with nanomolar potency. (A. E. Proudfoot et al., *J. Biol. Chem.* 1996 271:2599-2603). The severity of arthritis in rat adjuvant-induced arthritis was reduced by the administration of Met-RANTES. In addition, the levels of pro-inflammatory cytokines TNF-α and IL-1β. (S. Shahrara et al. *Arthr. & Rheum.* 2005 52:1907-1919) Met-RANTES has been shown to ameliorate the development of inflammation in an art recognized rodent model of inflammation, the collagen induced arthritis. (C. Plater-Zyberk et al. *Immunol. Lett.* 1997 57:117-120)

TAK-779 has also been shown to reduce both the incidence and severity of arthritis in the collagen-induced arthritis model. The antagonist inhibited the infiltration of inflammatory CCR5+ T-cells into the joint. (Y.-F. Yang et al., *Eur. J. Immunol.* 2002 32:2124-2132). Another CCR5 antagonist, SCH-X, was shown to reduce the incidence and severity of collagen-induced arthritis in rhesus monkeys. (M. P. M. Vierboom et al., *Arthr. & Rheum.* 2005 52(20):627-636).

In some anti-inflammatory conditions compounds of the present invention may be administered in combination with other anti-inflammatory drugs which may have a alternative mode of action. Compounds which may be combined with CCR5 antagonists include, but are not limited to:

(a) a lipoxygenase antagonist or biosynthesis inhibitor such as an inhibitor of 5-lipoxygenase, leukotriene antagonists (e.g., zafirlukast, montelukast, pranlukast, iralukast, pobilukast, SKB-106,203), leukotriene biosynthesis inhibitors (e.g., zileuton, BAY-1005);

(b) a non-steroidal antiinflammatory agent or cyclooxygenase (COX1 and/or COX2) inhibitor such as such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenarnic acid derivatives (flufenarnic acid, meclofenamic acid, mefenamic acid, niflumic acid and tolfenarnic acid), biphenylearboxylic acid derivatives (diflunisal and flufenisal), oxicarns (isoxicarn, piroxicam, sudoxicam and tenoxican), salicylates (acetyl salicylic acid, sulfasalazine), pyrazolones (apazone, bezpiperylon, feprazone, mofebutazone, oxyphenbutazone, phenylbutazone) and celecoxib;

(c) a TNF inhibitor such as infliximab (REMICADE®), etanercept (ENBREL®), or adalimumab (HUMIRA®);

(d) anti-inflammatory steroids such as beclomethasone, methylprednisolone, betamethasone, prednisone, dexamethasone, and hydrocortisone;

(e) immunomodulators such as cyclosporine, leflunomide (Arava®), azathioprine (Azasan®), penicillamine and levamisole;

(f) folate antagonists such as methotrexate;

(g) gold compounds such as aurothioglucose, gold sodium thiomalate or auranofin.

Methods for Treating Transplant Rejection

Rejection following solid organ transplantation also is characterized by infiltration of T-cells and macrophages expressing the CCR5 receptor into the interstitial area. (J. Pattison et al., *Lancet* 1994 343:209-211) Renal transplant patients homozygous for the CCR5Δ32 deletion a significant survival advantage of patients heterozygous for the CCR5Δ32 deletion or homozygous wild type patients. (M. Fischerder et al., *Lancet* 2001 357:1758-1761) CCR5$^{-/-}$ knockout mice showed significant prolong graft survival in after transplantation of heart and islet tissue. (W. Gao et al., *Transplantation* 2001 72:1199-1205; R. Abdi et al., *Diabetes* 2002 51:2489-2495. Blocking the CCR5 receptor activation has been found to significantly extend cardiac allograph survival. (W. W. Hancock et al., *Curr. Opin. Immunol.* 2003 15:479-486).

In treatment of transplant rejection or graft vs. host diseases CCR5 antagonists of the present invention may be administered in combination with other immunosuppressive agents including, but are not limited to, cyclosporine (SANDIMMUNE®), tacrolimus (PROGRAF®, FK-506), sirolimus (RAPAMUNE®, rapamycin), mycophenolate mofetil (CELLCEPT®), methotrexate, anti-IL-2 receptor (anti-CD25) antibodies such as daclizumab (ZENAPAX®) or basiliximab (SIMULECT®), anti-CD3 antibodies visilizumab (NUVION® or muromonab (OKT3, ORTHOCLONE®).

Methods for Treating Asthma and COPD

Antagonism of the CCR5 receptor has been suggested as a target to inhibit of progression of asthma and COPD by antagonism of Th1 activation: B. Ma et al., J. Immunol. 2006 176(8):4968-4978, B. Ma et al., *J. Clin. Investig.* 2005 115 (12):3460-3472 and J. K. L. Walker et al., *Am. J. Respir. Cell Mo. Biol.* 2006 34:711-718.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

The term "alkylene" as used herein denotes a divalent saturated linear hydrocarbon radical of 1 to 8 carbon atoms or a branched saturated divalent hydrocarbon radical of 3 to 8 carbon atoms, unless otherwise indicated. Examples of alkylene radicals include, but are not limited to, methylene, ethylene, propylene, 2-methyl-propylene, butylene and 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$. The term "alkoxyalkoxy" as used herein refers an alkoxy substituent in which one to three hydrogens are replaced by an alkoxy group. The term "alkoxy-imino" as used herein refer to a =NOR wherein R is an alkyl moiety as defined herein and the nitrogen forms a double bond attached to the substituted carbon.

The term "oxo" as use herein refers to a carbonyl (=O) group. Thus cyclohexane with an oxo substituent is cyclohexanone.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "cycloalkyl alkyl" as used herein refers to the radical R'R"-, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cyclolalkyl and R" is $C_{1-3}$ alkylene as defined herein.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term "arylcarbonyl" as used herein means a group of formula C(=O)R wherein R is an aryl group; the term "benzoyl" as used herein an "arylcarbonyl" group wherein R is phenyl.

The terms "alkoxycarbonyl" and "aryloxycarbonyl" as used herein denotes a group of formula —C(=O)OR wherein R is alkyl or aryl respectively and alkyl and aryl are as defined herein.

The term "haloalkyl" as used herein denotes a unbranched or branched chain alkyl group as defined above wherein 1, 2, 3 or more hydrogen atoms are substituted by a halogen. "$C_{1-3}$ haloalkyl" as used herein refers to an haloalkyl composed of 1 to 3 carbons and 1-8 halogen substituents. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl, 2,2,2-trifluoroethyl or difluoromethyl.

The term "$C_{1-6}$ fluoroalkyl" as used herein denotes a unbranched or branched chain alkyl group as defined above wherein 1, 2, 3 or more hydrogen atoms are substituted by a fluorine.

The terms "oxetanyl", "tetrahydrofuranyl" and "tetrahydropyranyl" refer to a four, five and six-membered non-fused heterocyclic ring respectively, each containing one oxygen atom. The term "pyridine" refers to a six-membered heteroaromatic ring with one nitrogen atom. The terms "pyrimidine", "pyrazine" and "pyridazine" refer to a six-membered nonfused heteroaromatic ring with two nitrogen atoms disposed in a 1,3, a 1,4 and a 1,2 relationship respectively.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-Azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), $MeSO_2$-(mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-Bu$Me_2$Si (TBDMS), triethylamine (TEA or $Et_3N$), 2,2,6,6-tetramethylpiperidine 1-oxyl (TEMPO), triflate or $CF_3SO_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

The symbols "*" at the end of a bond or "------" drawn through a bond each refer to the point of attachment of a functional group or other chemical moiety to the rest of the molecule of which it is a part. Thus, for example:

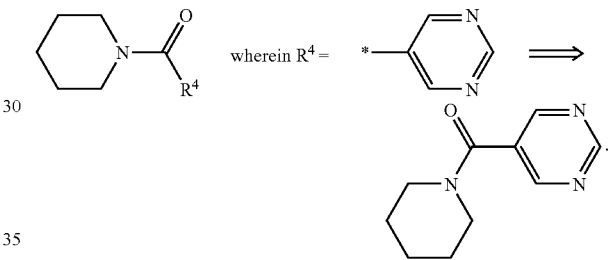

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I (I)

| Cpd. No. | $R^1$ | $R^4$ | $C5^1$ | mw | ms | mp |
|---|---|---|---|---|---|---|
| I-1 | MeO... | Me... | RS | 583.81 | 584 | |

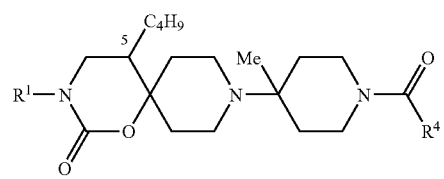

TABLE I-continued (I)

| Cpd. No. | R¹ | R⁴ | C5¹ | mw | ms | mp |
|---|---|---|---|---|---|---|
| I-2 | trans-4-MeO-cyclohexyl-CH₂* | 4,6-dimethylpyrimidin-5-yl | S | 583.81 | 584 | |
| I-3 | cis-4-MeO-cyclohexyl-CH₂* | 4,6-dimethylpyrimidin-5-yl | S | 583.81 | 584 | 150.8-152.9 |
| I-4 | cis-4-HO-cyclohexyl-CH₂* | 4,6-dimethylpyrimidin-5-yl | S | 569.79 | 570 | |
| I-5 | trans-4-HO-cyclohexyl-CH₂* | 4,6-dimethylpyrimidin-5-yl | S | 569.79 | 570 | |
| I-6 | trans-4-EtO-cyclohexyl-CH₂* | 4,6-dimethylpyrimidin-5-yl | S | 597.84 | 598 | |
| I-7 | cis-4-EtO-cyclohexyl-CH₂* | 4,6-dimethylpyrimidin-5-yl | S | 597.84 | 598 | 188.3-189.7 |
| I-8 | trans-4-(MeOCH₂O)-cyclohexyl-CH₂* | 4,6-dimethylpyrimidin-5-yl | S | 613.84 | 614 | |

TABLE I-continued (I)

| Cpd. No. | R¹ | R⁴ | C5¹ | mw | ms | mp |
|---|---|---|---|---|---|---|
| I-9 | (trans-4-(methoxymethoxy)cyclohexyl)methyl | 4,6-dimethylpyrimidin-5-yl | S | 613.84 | 614 | |
| I-10 | (trans-4-hydroxycyclohexyl)methyl | 6-cyano-2,4-dimethylpyridin-3-yl | S | 593.81 | 594 | |

TABLE II (I)

| Cpd. No. | R¹ | R⁴ | C5¹ | mw | ms | mp |
|---|---|---|---|---|---|---|
| II-1 | (3-oxabicyclo[3.1.0]hexan-6-yl)methyl | 4,6-dimethylpyrimidin-5-yl | S | 553.74 | 554 | |
| II-2 | (3-oxabicyclo[3.1.0]hexan-6-yl)methyl | 6-cyano-2,4-dimethylpyridin-3-yl | S | 577.77 | 578 | |
| II-3 | (3-oxabicyclo[3.1.0]hexan-6-yl)methyl | 4,6-dimethyl-2-(trifluoromethyl)pyrimidin-5-yl | S | 621.44 | 622 | |

TABLE II-continued (I)

| Cpd. No. | R¹ | R⁴ | C5¹ | mw | ms | mp |
|---|---|---|---|---|---|---|
| II-4 | [1R,5S,6S]-6-(ethyl*)-3-oxabicyclo[3.1.0]hexane | 2,4-dimethyl-6-(CHF₂)-pyridin-3-yl* | S | 602.76 | 603 | |
| II-5 | hexahydrofuro[2,3-b]furan-3-yl-methyl* | 4,6-dimethylpyrimidin-5-yl* | S | 583.77 | 584 | |
| II-6 | hexahydrofuro[2,3-b]furan-3-yl-methyl* | 4,6-dimethylpyrimidin-5-yl* | S | 583.77 | 584 | |
| II-7 | hexahydrofuro[2,3-b]furan-3-yl-methyl* | 2,4-dimethyl-6-CN-pyridin-3-yl* | S | 607.79 | 608 | |
| II-8 | hexahydrofuro[2,3-b]furan-3-yl-methyl* | 2,4-dimethylpyridin-3-yl* | RS | 582.78 | 583 | |
| II-9 | (1,4-dioxan-2-yl)methyl* | 4,6-dimethylpyrimidin-5-yl* | S | 557.73 | 558 | |
| II-10 | (1,4-dioxan-2-yl)methyl* | 2,4-dimethyl-6-CN-pyridin-3-yl* | S | 581.75 | 582 | |

TABLE II-continued (I)

| Cpd. No. | R¹ | R⁴ | C5¹ | mw | ms | mp |
|---|---|---|---|---|---|---|
| II-11 | 1,4-dioxan-2-yl-methyl (S) | 4,6-dimethylpyrimidin-5-yl | S | 557.73 | 558 | |
| II-12 | 1,4-dioxan-2-yl-methyl (S) | 2,4-dimethyl-6-cyanopyridin-3-yl | S | 581.75 | 582 | |
| II-13 | (1-fluoro-3-oxabicyclo[3.1.0]hex-1-yl)methyl | 4,6-dimethylpyrimidin-5-yl | S | 571.73 | 572 | |

TABLE III (I)

| Cpd. No. | R¹ | R⁴ | C5¹ | mw | ms | mp |
|---|---|---|---|---|---|---|
| III-1 | (1-acetylpiperidin-4-yl)methyl | 4,6-dimethylpyrimidin-5-yl | RS | 596.81 | 597 & 619 | |
| III-2 | (1-acetylpiperidin-3-yl)ethyl | 4,6-dimethylpyrimidin-5-yl | RS | 624.87 | 625 | |

TABLE III-continued
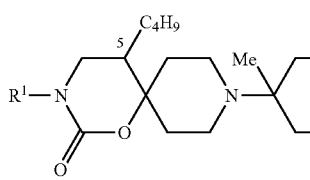
(I)
| Cpd. No. | R¹ | R⁴ | C5¹ | mw | ms | mp |
|---|---|---|---|---|---|---|
| III-3 | i-Pr 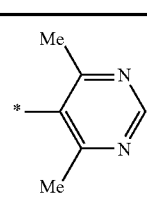 | Me 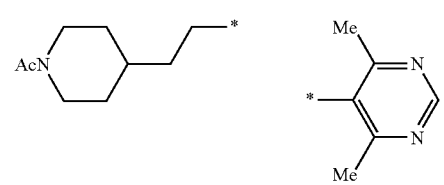 Me | RS | 610.84 | 611 | |
| III-4 | 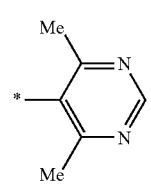 | Me 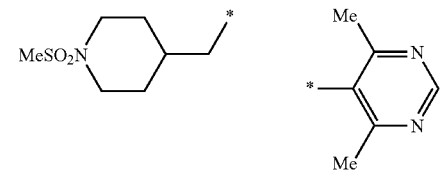 Me | RS | 632.87 | 633 | |
| III-5 | 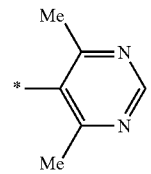 | Me 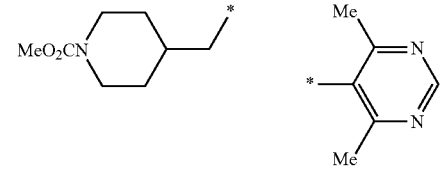 Me | S | 612.81 | 613 | 125.0-128.0 |
| III-6 | 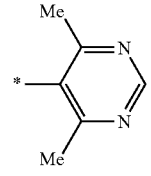 | Me 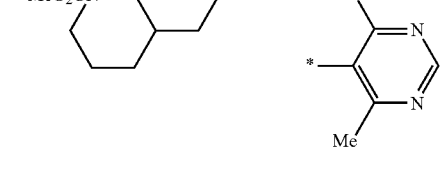 Me | RS | 612.81 | 613 | |
| III-7 | 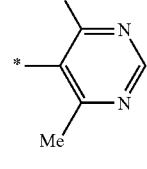 | Me 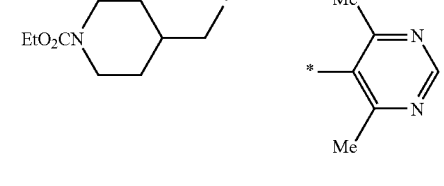 Me | S | 626.84 | 627 & 649 | 102.7-105 |
| III-8 | 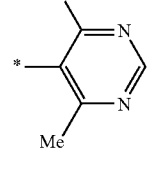 | Me 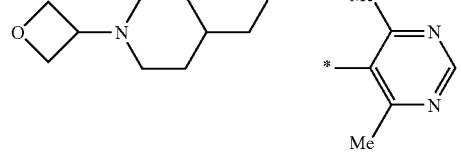 Me | S | 610.84 | 611 | |
| III-9 | 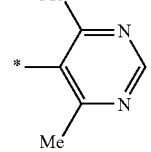 | Me 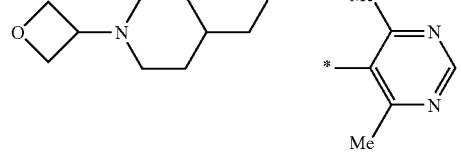 Me | S | 594.84 | 595 | |

TABLE III-continued (I)

| Cpd. No. | R¹ | R⁴ | C5¹ | mw | ms | mp |
|---|---|---|---|---|---|---|
| III-10 | cyclopropyl-N-piperidinyl-CH₂-* | 4,6-dimethylpyrimidin-5-yl | S | 618.81 | 619 & 641 | |
| III-11 | F₂CH-CH₂-N-piperidinyl-CH₂-* | 4,6-dimethylpyrimidin-5-yl | S | 642.83 | 643 | |
| III-12 | F₂CH-CH₂-N-piperidinyl-CH₂-* | 2,4-dimethyl-6-cyanopyridin-3-yl | RS | 616.84 | 617 | |
| III-13 | EtO₂C-N-pyrrolidin-3-yl-CH₂-* | 4,6-dimethylpyrimidin-5-yl | S | 612.81 | 613 | |
| III-14 | MeO₂C-N-pyrrolidin-3-yl-CH₂-* | 4,6-dimethylpyrimidin-5-yl | S | 598.78 | 599 | |
| III-15 | F₂HCCH₂-N-pyrrolidin-3-yl-CH₂-* | 4,6-dimethylpyrimidin-5-yl | S | 604.78 | 605 | |
| III-16 | MeO₂C-N-azabicyclo-CH₂-* | 4,6-dimethylpyrimidin-5-yl | S | 624.82 | 625 | |

TABLE III-continued (I)

| Cpd. No. | R¹ | R⁴ | C5¹ | mw | ms | mp |
|---|---|---|---|---|---|---|
| III-17 | EtO₂CN-[bicyclic with H's]-* | 4,6-dimethylpyrimidin-5-yl | S | 624.82 | 625 | |
| III-18 | i-PrO₂CN-[bicyclic with H's]-* | 4,6-dimethylpyrimidin-5-yl | S | 638.85 | 639 | |
| III-19 | F₂HCH₂CN-[bicyclic with H's]-* | 4,6-dimethylpyrimidin-5-yl | S | 616.79 | 617 | |
| III-20 | MeO₂CN-[bicyclic with H's]-* | 3-Me-5-CF₃-isoxazol-4-yl | S | 653.74 | 654 | |
| III-21 | AcN-[bicyclic with H's]-* | 3-Me-5-CF₃-isoxazol-4-yl | S | 637.74 | 638 | |
| III-22 | MeO₂CN-[bicyclooctyl]-* | 4,6-dimethylpyrimidin-5-yl | S | 622.85 | 623 | |
| III-23 | MeSO₂N-[piperidinyl-CH₂]-* | 3-Me-5-CF₃-isoxazol-4-yl | S | 675.85 | 676 | |
| III-24 | MeO₂CN-[piperidinyl-CH₂]-* | 3-Me-5-CF₃-isoxazol-4-yl | S | 655.75 | 656 | |

TABLE III-continued (I) Structure: R¹-N(C(=O)O-)-spiro-C₄H₉(5)-piperidine-N-C(Me)-piperidine-N-C(=O)-R⁴

| Cpd. No. | R¹ | R⁴ | C5¹ | mw | ms | mp |
|---|---|---|---|---|---|---|
| III-25 | AcN-piperidine-CH₂-* | 3-Me-5-CF₃-isoxazol-4-yl-* | S | 639.76 | 640 | |
| III-26 | AcN-piperidine(3-yl)-CH₂-* | 3-Me-5-CF₃-isoxazol-4-yl-* | RS | 596.81 | 597 & 619 | |

TABLE IV (I) Structure: R¹-N(C(=O)O-)-spiro-C₄H₉(5)-piperidine-N-C(Me)-piperidine-N-C(=O)-R⁴

| Cpd. No. | R¹ | R⁴ | C5¹ | mw | ms | mp |
|---|---|---|---|---|---|---|
| IV-1 | 3,3-difluorocyclobutyl-CH₂-* | 4,6-dimethylpyrimidin-5-yl-* | RS | 561.71 | 562 | |
| IV-2 | 4-oxocyclohexyl-CH₂-* | 4,6-dimethylpyrimidin-5-yl-* | S | 567.77 | 568 | |
| IV-3 | 4-cyanophenyl-CH₂-* | 4,6-dimethylpyrimidin-5-yl-* | RS | 572.75 | 573 | |
| IV-4 | 1-Me-4-HO-cyclohexyl-CH₂-* | 4,6-dimethylpyrimidin-5-yl-* | S | 583.81 | 584 | |

TABLE IV-continued (I)

| Cpd. No. | R¹ | R⁴ | C5¹ | mw | ms | mp |
|---|---|---|---|---|---|---|
| IV-5 | pyrimidin-2-ylmethyl | 2,3-dimethylpyridin-4-yl* | S | 548.73 | 549 | |
| IV-6 | (4,6-dimethylpyrimidin-5-yl)methyl | 6-cyano-2,4-dimethylpyridin-3-yl* | S | 601.79 | 602 | |
| IV-7 | 4,4-difluorocyclohexyl | 4,6-dimethylpyrimidin-5-yl* | S | 575.74 | 576 | |
| IV-8 | pyridin-2-yl* | 4,6-dimethylpyrimidin-5-yl* | S | 534.70 | 535 | |
| IV-9 | pyridin-2-yl* | 6-cyano-2,4-dimethylpyridin-3-yl* | S | 558.72 | 559 | |
| IV-10 | 2-(tetrahydropyran-4-yl)ethyl* | 4,6-dimethylpyrimidin-5-yl* | S | 569.79 | 570 | 92.0-94.7 |
| IV-11 | (4-(methoxyimino)cyclohexyl)methyl* | 4,6-dimethylpyrimidin-5-yl* | S | 596.81 | 597 | |

TABLE IV-continued (I)

[Structure of compound class I shown with R¹—N, C₄H₉ at position 5, Me, N, O, R⁴ substituents on fused ring system]

| Cpd. No. | R¹ | R⁴ | C5[1] | mw | ms | mp |
|---|---|---|---|---|---|---|
| IV-12 | EtON=[cyclohexyl-CH₂-*] | 4,6-dimethylpyrimidin-5-yl | S | 610.84 | 610 | |
| IV-13 | tetrahydropyran-4-yl | 4,6-dimethylpyrimidin-5-yl | S | 541.73 | 542 | |
| IV-14 | F₂CHCH₂— | 2,4-dimethyl-6-cyanopyridin-3-yl | S | 545.67 | 546 | |

[1] Configuration at C5- RS = racemic

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

SCHEME A

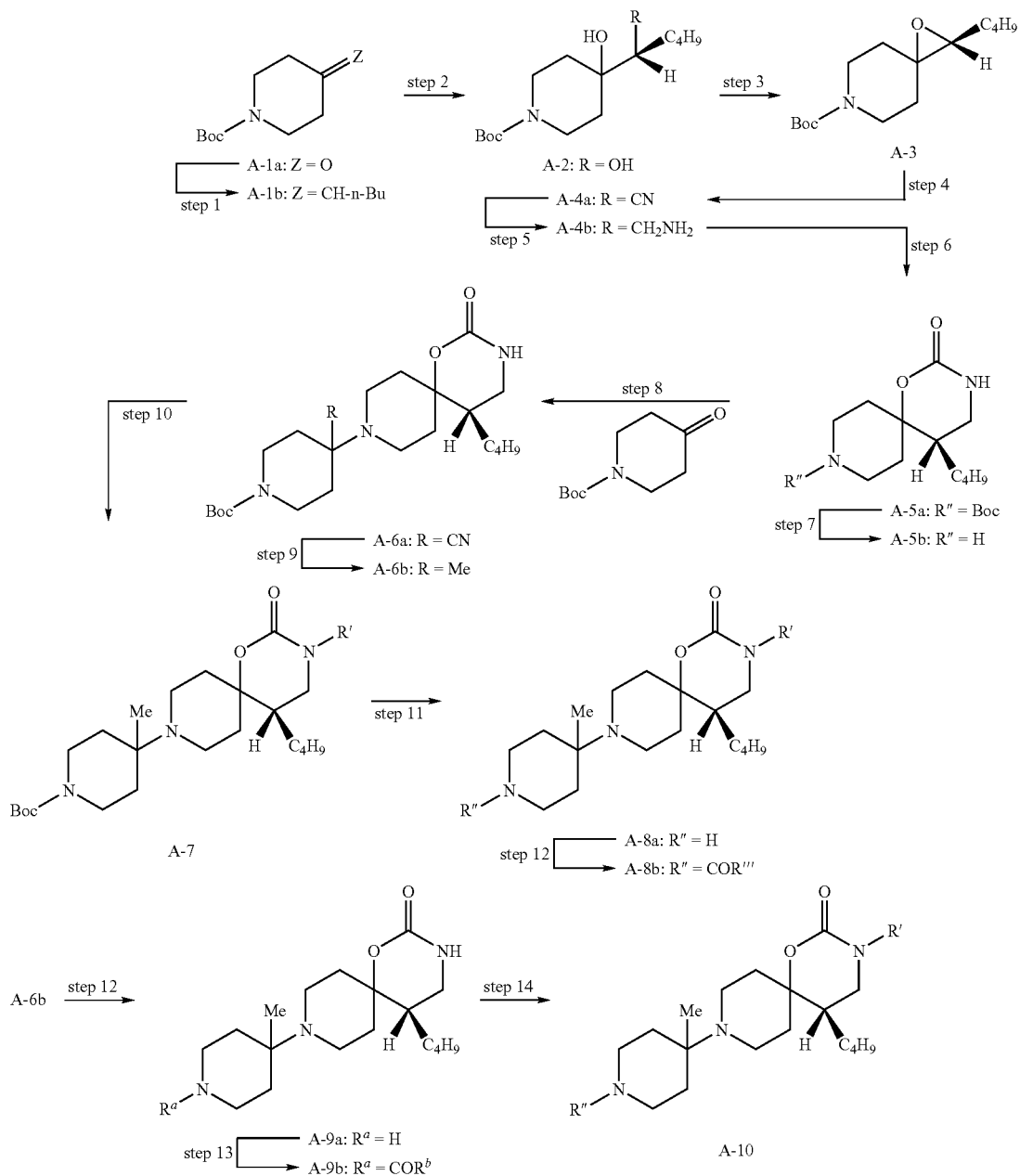

The chiral synthesis of A-6b (SCHEME A) was achieved utilizing a procedure analogous to that described for S. D. Gabriel and D. M. Rotstein in U.S. Pat. Pub. 20050176703. The trisubstituted olefinic precursor A-1b was prepared by Wittig olefination of A-1a with pentylidene-triphenyl-$\lambda^5$-phosphane. Asymmetric dihydroxylation of A-1b was carried out with AD-mix-β which consists of a premix containing of $K_3Fe(CN)_6$, $K_2CO_3$, $K_2O_sO_2(OH)_4$ and hydroquinidine 1,4-diphthalazinediyl diether. Asymmetric hydroxylation is well known in the art, e.g., H. C. Kolb et al. Chem. Rev. 1994 94:2483-2547, K. B. Sharpless et al. J. Org. Chem. 1992 57:2768-2771. The resulting asymmetric diol A-2 was selectively mesylated on the secondary alcohol and converted to epoxide A-3. Epoxide-opening mediated by $Et_3AlCN$ afforded the hydroxynitrile A-4-a which was reduced to amino alcohol A-4-b and cyclized with phosgene to yield A-5a which contains the C-5 in the S-configuration.

The 4-methyl-N-Boc-piperidine moiety was introduced by removal of the protecting group with TFA/DCM to afford A-5b. Removal of a Boc protecting group is accomplished using acidic conditions, typically by treatment with TFA and DCM or HCl and dioxane. $Ti(O-i-Pr)_4$ mediated condensation of the secondary amine with N-Boc-4-oxo-piperidine and trapping the intermediate imine with $Et_2AlCN$ afforded A-6a which was subsequently converted to A-6b by displacing the nitrile with methyl magnesium bromide to afford A-6b (A. Palani et al. *J. Med. Chem.* 2001 44(21):3339-42).

Compounds of present invention typically contain a moiety on the carbamoyl nitrogen which is introduced by N-alkylation of the carbamate. The alkylating agents are prepared by methodology well known in the art starting from commercially available compounds or compounds which are described in the literature. Typically an alcohol is available or can be prepared by reduction of a carboxylic acid derivatives. Such reductions are standard functional group transformations. The alcohol is then displaced with a halide or sulfonylated with tosyl chloride or mesyl chloride. Representative alkylating agents and conditions for the alkylation can be found in the examples which follow which are exemplary and not limiting. Alkylation of carbamates is typically carried out in solvents like DMF, NMP, MeCN, acetone, DCM and DCE at temperatures between 0° C. and 100° C. Typically used bases include, but are not limited to, $K_2CO_3$, NaH, lithium hexamethyldisilazide, sodium hexamethyldisilazide and potassium hexamethyldisilazide. In instances where the N-alkyl substituents contain asymmetric carbons, the present invention includes both stereoisomers and mixtures thereof. Procedures to prepare the carbamoyl nitrogen substituents can be found in the literature or in the examples that follow.

Introduction of the amide onto the piperidine nitrogen was accomplished by condensation of the secondary amine with an activated carboxylic acid. Carboxylic acid activating agents including, but not limited to, EDCI or DCC, with or without HOBt or bases including but not limited to TEA or DIPEA in an inert solvent such as DMF, THF or DCM at temperatures between 0° C. and 60° C. can be employed. The reaction may alternatively be carried out in presence of O-(7-azabenzotriazol-1-yl)-N,N,N',N'-tetramethyluronium hexafluorophosphate (HATU) or 1-hydroxy-7-azabenzotriazole (HOAt). (J. March, *Advanced Organic Chemistry*, John Wiley & Sons: New York, N.Y., 1992, pp. 417-425; H. G. Benz, *Synthesis of Amides and Related Compounds in Comprehensive Organic Synthesis*, E. Winterfeldt, ed., vol. 6, Pergamon Press, Oxford 1991 pp. 381-411).

One skilled in the art will recognize that the N-alkylation/deprotection/acylation sequence can be readily modified to deprotection/acylation/N-alkylation without departing from the methodology described herein. The latter sequence is illustrated in steps 12-14 of SCHEME A and the choice is dictated by operator convenience.

Biological Assays

The capacity for novel compounds of the present invention to bind to the CCR5 receptor and thereby antagonize CCR5 function can be evaluated with assay systems known in the art. The capacity of compounds of the present invention to inhibit infection of $CD4^+/CCR5^+$ expressing cells can be determined using a cell-cell fusion assay as described in example 8 or an antiviral assay as described in example 9.

Functional assays directly measure the ability of a compound to produce a biologically relevant response or inhibit a response produced by a natural ligand (i.e., distinguish agonist vs. antagonist properties of the test compounds). In a calcium flux assay, cells expressing the CCR5 are loaded with calcium sensitive dyes prior to addition of compound or the natural CCR5 ligand. Compounds with agonist properties will induce a calcium flux signal in the cell, while the compounds of this invention are identified as compounds which do not induce signaling by themselves but are capable of blocking signaling by the natural ligand RANTES.

The chemotaxis assay is a functional assay which measures the ability of a non-adherent cell line expressing human CCR5 receptor to migrate across a membrane in response to either test compounds or natural attractant ligand(s) (i.e., RANTES, MIP-1β). Generally, chemotaxis assays monitor the directional movement or migration of a suitable cell (such as a leukocyte (e.g., lymphocyte, eosinophil, basophil)) into or through a barrier (e.g., endothelium, a permeable filter membrane), toward, from a first surface of the barrier toward an opposite second surface containing attractant ligands. Membranes or filters provide convenient barriers to monitor the directional movement or migration of a suitable cell into or through a filter, toward increased levels of an attractant. In some assays, the membrane is coated with a substance to facilitate adhesion, such as ICAM-1, fibronectin or collagen. Such assays provide an in vitro approximation of leukocyte "homing". Compounds that are antagonists not only fail to induce chemotaxis, but are also capable of inhibiting cell migration in response to known CCR5 ligands.

A suitable membrane, having a suitable pore size for monitoring specific migration in response to compound, including, for example, nitrocellulose, polycarbonate, is selected. For example, pore sizes of about 3-8 microns, and preferably about 5-8 microns can be used. The pore size can be uniform on a filter or within a range of suitable pore sizes.

To assess migration and inhibition of migration, the distance of migration into the filter, the number of cells crossing the filter that remain adherent to the second surface of the filter, and/or the number of cells that accumulate in the second chamber can be determined using standard techniques (e.g., microscopy). In one embodiment, the cells are labeled with a detectable label (e.g., radioisotope, fluorescent label, antigen or epitope label), and migration can be assessed in the presence and absence of the antibody by determining the presence of the label adherent to the membrane and/or present in the second chamber using an appropriate method (e.g., by detecting radioactivity, fluorescence, immunoassay).

In a more physiologically relevant variation of a chemotaxis assay, particularly for T cells, monocytes or cells expressing a mammalian CCR5, transendothelial migration is monitored. Such assays mimic leukocytes migration from blood vessels toward chemoattractants present in the tissues at sites of inflammation by crossing the endothelial cell layer lining the vessel wall.

Endothelial cells can be cultured and form a confluent layer on a microporous filter or membrane, optionally coated with a substance such as collagen, fibronectin, or other extracellular matrix proteins, to facilitate the attachment of endothelial cells. A variety of mammalian endothelial cells can are available for monolayer formation, including for example, vein, artery or microvascular endothelium. Generally, the assay is performed by detecting the directional migration of cells into or through a membrane or filter.

In a composition comprising cells capable of migration and expressing a mammalian CCR5 receptor can be placed in the first chamber. A composition comprising one or more natural attractant ligands capable of inducing chemotaxis of the cells in the first chamber is placed in the second chamber. Preferably shortly before the cells are placed in the first chamber, or simultaneously with the cells, a composition comprising the compound to be tested is placed, preferably, in the first chamber. Compounds which can bind receptor and inhibit the induction of chemotaxis by natural attractant ligands, of the cells expressing a mammalian CCR5 are inhibitors of receptor function. A reduction in the extent of migration induced by the ligand or promoter in the presence of the antibody is indicative of inhibitory activity.

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It should be understood that all references to pharmaceutically acceptable salts include solvent addition forms (solvates) or crystal forms (polymorphs) as defined herein, of the same acid addition salt.

"Pharmaceutically acceptable" means that the moiety is useful in preparing a pharmaceutical composition that is generally safe, non-toxic, and neither biologically nor otherwise undesirable.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with one or more antiviral agents, such as a nucleoside reverse transcriptase inhibitor, another nonnucleoside reverse transcriptase inhibitor, a HIV protease inhibitor or a viral entry inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

The methods of the present invention are intended for use with any mammal that may experience the benefits of the methods of the invention. Foremost among such mammals are humans, although the invention is not intended to be so limited, and is applicable to veterinary uses. Thus, in accordance with the invention, "mammals" or "mammal in need" include humans as well as non-human mammals, particularly domesticated animals including, without limitation, cats, dogs, and horses.

EXAMPLE 1

5-Butyl-3-(3,3-difluoro-cyclobutylmethyl)-9-[1-(4,6-dimethyl-pyrimidine-5-carbonyl)-4-methyl-piperidin-4-yl]-1-oxa-3,9-diaza-spiro[5.5]undecan-2-one (IV-I, SCHEME A)

step a-1 (3,3-Difluoro-cyclobutyl)-methanol (20)—To a slurry of NaBH (55 mg, 1.47 mmol) in THF (5 mL) cooled to 0° C. was added dropwise a solution of 3,3-difluoro-cyclobutanecarboxylic acid (CASRN 107496-54-8, 0.2 g, 1.47 mmol) in TIE (5 mL). The reaction mixture was stirred for 1 h, cooled to 0° C. and $BF_3.Et_2O$ (0.18 mL) was added. The reaction mixture was stirred for 18 h at RT, cooled to 0° C. then quenched by dropwise addition of 95% EtOH. After 1 h the solvents were evaporated in vacuo, the residue was partitioned between DCM and brine. The organic layer was dried ($MgSO_4$), filtered and concentrated to afford 0.12 g of (3,3-difluoro-cyclobutyl)-methanol (22).

step b-2 Toluene-4-sulfonic acid 3,3-difluoro-cyclobutylmethyl ester (24)—To a solution of 22 (0.12 g, 0.98 mmol) and pyridine (3 mL) cooled to 0° C., was added p-toluenesulphonyl chloride (0.3 g, 1.57 mmol) in several portions. The reaction mixture was stirred at RT for 18 h, poured into 10 mL of ice-water and thrice extracted with DCM (3×10 mL). The combined organic extracts were dried ($MgSO_4$), filtered and concentrated in vacuo. The product was purified by $SiO_2$ chromatography eluting with EtOAc/hexane (1:10) to afford 0.1 g of 24.

step 12—A solution of A-6b (2.5802 g, 6.1 mmol), TFA (1.7 mL, 61 mmol) and DCM (25 mL) was stirred for overnight at RT then concentrated in vacuo. The residue was triturated with toluene and re-evaporated. The residue was partitioned between 2M NaOH and EtOAc. The organic layer was isolated and the aqueous layer was concentrated to half its volume, treated with solid NaCl then back-extracted three times with EtOAc. The combined organics were washed with brine and dried ($MgSO_4$) to afford 1.3 g (67% yield) of A-9a as an off-white foam: MS $[M+H]^+$ 324 and $[2M+H]^+$ 647.

step 13—To a solution of A-9a (1.32 g, 4 mmol) and 4,6-dimethyl-pyrimidine-5-carboxylic acid (0.745 g, 5 mmol) and DMF (10 mL) were added sequentially HOBt (0.717 g, 5 mmol), EDCI (1.017 g, 5 mmol) and DIPEA (2.1 mL, 12 mmol). The reaction mixture was stirred at RT for 72 h. The solvent was removed under high vacuum and the residue was suspended in EtOAc and treated with a small amount of saturated $NaHCO_3$. The aqueous layer was back-extracted three times with EtOAc and the combined organic phases were washed with brine, dried ($MgSO_4$), filtered and evaporated. The crude product was purified by $SiO_2$ chromatography eluting with a DCM/MB gradient (100-60% DCM; MB=DCM/MeOH/$NH_4OH$, 60:10:1) to afford 0.90 g (48%) of A-9b ($R^a$=4,6-dimethyl-pyrimidin-5-yl) as a white foam: MS $[M+H]^+$=458.

step 14—To a solution of A9-b from step 13 (80 mg, 0.175 mmol) in DMF (2 mL) was added NaH (7 mg, 0.29 mmol). After stirring for 15 min, a solution of 24 (100 mg, 0.36 mmol) and DMF (1 mL) was added, and resulting mixture was stirred at RT for 18 h. The DMF was removed in vacuo and the residue was partitioned between EtOAc and water. The organic layer was dried ($MgSO_4$), filtered and concentrated in vacuo. The reissue was purified by $SiO_2$ chromatography eluting with MeOH/DCM (1:10) to afford 10 mg of IV-1: $M^+$=562.

EXAMPLE 2

5-Butyl-9-[1-(4,6-dimethyl-pyrimidine-5-carbonyl)-4-methyl-piperidin-4-yl]-3-(trans-3-methoxy-cyclohexylmethyl)-1-oxa-3,9-diaza-spiro[5.5]undecan-2-one (I-1)

(3-Methoxy-cyclohexyl)-methanol (26)—Prepared from 3-methoxy-cyclohexanecarboxylic acid (1.2 g, 7.59 mmol) as described in step a of example 1 to afford 1 g (90%) of 26.

trans-Toluene-4-sulfonic acid 3-methoxy-cyclohexylmethyl ester (28)—Prepared from 26 (1 g, 6.9 mmol) as described in step b of example 1. The cis- and trans-isomers were separated by $SiO_2$ chromatography eluting with EtOAc/hexane (1:4) to afford 150 mg of trans-toluene-4-sulfonic acid 3-methoxy-cyclohexylmethyl ester and 150 mg of 28.

step 10—To a solution of A-6b (0.21 g, 0.5 mmol) in DMF (3 mL) was added NaH (30 mg) and the resulting suspension stirred for 15 min. A solution of 28 (150 mg, 0.5 mmol) was added, and resulting mixture was stirred at RT for 18 h. The DMF was removed in vacuo and the residue was partitioned between EtOAc and water. The organic layer was dried ($MgSO_4$), filtered and concentrated. The residue was purified by $SiO_2$ chromatography eluting with MeOH/DCM (1:10) to afford 130 mg of A-7 (R'=trans-3-methoxy-cyclohexylmethyl).

step 11—A solution of A-7 from step 10 (130 mg, 0.23 mmol) TFA (1 mL) and DCM (5 mL) was stirred for 1 h then concentrated in vacuo. The residue was dissolved in DCM (20 mL) which washed with saturated $Na_2CO_3$ (3×5 mL). The organic layer was dried ($MgSO_4$), filtered, concentrated and dried in vacuo to afford 80 mg of A-8a (R'=trans-3-methoxy-cyclohexylmethyl).

step 12—To a solution of A-8a from step 11 (80 mg, 0.178 mmol), 4,6-dimethyl-pyrimidine-5-carboxylic acid (50 mg, 0.33 mmol) and HOBT (45 mg, 0.33 M) in DMF (2 mL) was added EDCI (63 mg, 0.33 mmol) followed by DIPEA (0.15 mL). The reaction mixture was stirred at 40° C. for 4 h, then at RT for 18 h and finally concentrated in vacuo. The residue was diluted with EtOAc (80 mL), washed with 1N NaOH (10 mL) followed by brine (10 mL). The organic layer was dried ($MgSO_4$), filtered and concentrated. The residue was purified by $SiO_2$ chromatography eluting with MeOH/DCM (1:10) to afford 25 mg of I-1: $M^+$=584.

I-2 was prepared analogously ($M^+$=584) except in step 10, cis-toluene-4-sulfonic acid 3-methoxy-cyclohexylmethyl ester was used in place of trans-toluene-4-sulfonic acid 3-methoxy-cyclohexylmethyl ester.

EXAMPLE 3

5-Butyl-9-[1-(4,6-dimethyl-pyrimidine-5-carbonyl)-4-methyl-piperidin-4-yl]-3-(trans-4-methoxy-cyclohexylmethyl)-1-oxa-3,9-diaza-spiro[5.5]undecan-2-one (I-3)

Cis- and trans-toluene-4-sulfonic acid 4-methoxy-cyclohexylmethyl ester (30) were prepared from 4-methoxy-cyclohexanecarboxylic acid as described in example 2. The cis- and trans-isomers were separated by $SiO_2$ chromatography eluting with EtOAc/hexane (1:4).

I-3 ($M^+$=584) was prepared from A-6b as described in steps 10-12 of example 2 except in step 10, trans-toluene-4-sulfonic acid 3-methoxy-cyclohexylmethyl ester was replaced with trans-30.

5-Butyl-9-[1-(4,6-dimethyl-pyrimidine-5-carbonyl)-4-methyl-piperidin-4-yl]-3-(cis-4-methoxy-cyclohexylmethyl)-1-oxa-3,9-diaza-spiro[5.5]undecan-2-one was prepared analogously except in step 10, trans-toluene-4-sulfonic acid 4-methoxy-cyclohexylmethyl ester was replaced with cis 30 to afford I-2: $M^+$=584.

5-Butyl-9-[1-(4,6-dimethyl-pyrimidine-5-carbonyl)-4-methyl-piperidin-4-yl]-3-(trans-4-ethoxy-cyclohexylmethyl)-1-oxa-3,9-diaza-spiro[5.5]undecan-2-one and 5-butyl-9-[1-(4,6-dimethyl-pyrimidine-5-carbonyl)-4-methyl-piperidin-4-yl]-3-(cis-4-ethoxy-cyclohexylmethyl)-1-oxa-3,9-diaza-spiro[5.5]undecan-2-one were prepared analogously except 30 was replaced by trans- and cis-4-ethoxy-cyclohexanecarboxylic acid ethyl ester to afford I-7 ($M^+$=598) and I-6 ($M^+$=598), respectively. The cis and trans-tosylates were separated by $SiO_2$ chromatography.

EXAMPLE 4

5-Butyl-9-[1-(4,6-dimethyl-pyrimidine-5-carbonyl)-4-methyl-piperidin-4-yl]-3-(cis-4-methoxymethoxy-cyclohexylmethyl)-1-oxa-3,9-diaza-spiro[5.5]undecan-2-one (I-8)

3 Toluene-4-sulfonic acid 4-methoxymethoxy-cyclohexylmethyl ester

4-Methoxymethoxy-cyclohexanecarboxylic acid ethyl ester (32)—To a solution of 4-hydroxy-cyclohexanecarboxylic acid ethyl ester (1 g, 5.8 mmol) and DIPEA (4.2 mL, 0.024 mol) was added chloro-methoxy-methane (1.89 g, 0.0235 mol). The reaction mixture was stirred overnight at RT then concentrated in vacuo. The residue was dissolved in DCM (50 mL), washed with water (2×10 mL), dried (MgSO$_4$), filtered and concentrated to afford 1.2 g of 32.

(4-Methoxymethoxy-cyclohexyl)-methanol (34)—To a solution of 32 (1.2 g, 5.5 mmol) and THF (30 mL) cooled to −20° C., was added dropwise a solution of LiAlH$_4$ in THF (1M solution, 16.5 mL). Stirring was continued at −20° C. for 1 h, then warmed to RT and stirred for 18 h. The reaction mixture was cooled to −5° C., quenched with 20% aqueous NaHSO$_4$, stirred at RT for 1 h, diluted with EtOAc (50 mL) and stirred for 30 min. The resulting precipitate was filtered, the solvents evaporated and the residue dried in vacuo to afford 0.95 g of 34.

Toluene-4-sulfonic acid 4-methoxymethoxy-cyclohexylmethyl ester (36)—Prepared from 34 (0.95 g, 5.4 mmol) and p-toluenesulfonyl chloride (1.3 g, 7 mmol) as described in example 1. The cis- and trans-isomers were separated by $SiO_2$ chromatography eluting with EtOAc/hexane (1:4) to afford the cis and trans tosylates.

I-8 ($M^+$=614) and I-9 ($M^+$=614) were prepared from A-9b ($R^b$=4-methoxymethoxy-cyclohexylmethyl) as described in step 14 of example 1 except difluorocyclobutyl methoxy tosylate was replaced by either cis 36 or trans 36.

EXAMPLE 5

5-Butyl-9-[1-(4,6-dimethyl-pyrimidine-5-carbonyl)-4-methyl-piperidin-4-yl]-3-(trans-4-hydroxy-cyclohexylmethyl)-1-oxa-3,9-diaza-spiro[5.5]undecan-2-one (I-4)

4-(tert-Butyl-dimethyl-silanyloxy)-cyclohexanecarboxylic acid ethyl ester (38)—To a solution of 4-oxy-cyclohexanecarboxylic acid ethyl ester (CASRN 17159-80-7, 1.7 g, 0.01 mol) in DMF (14 mL) was added DMAP (58 mg, 0.47 mmol), TEA (1.54 mL) and tert-butyl-dimethylsilyl chloride (1.65 g, 0.011 mol). The reaction mixture was stirred at RT for 18 h, poured into ice (10 g), extracted with EtOAc (3×50 mL). The organic extracts were dried (MgSO$_4$) filtered and concentrated. The residue was purified by $SiO_2$ chromatography eluting with EtOAc/hexane (1:20) to afford 2.25 g (79%) of 4-(tert-butyl-dimethyl-silanyloxy)-cyclohexanecarboxylic acid ethyl ester (38) as colorless oil.

The ester 38 was reduced to the alcohol and converted to the tosylate 40 as described in example 1. The cis- and trans-isomers were separated by $SiO_2$ chromatography eluting with EtOAc/hexane (1:20).

5-Butyl-3-[trans-4-(tert-butyl-dimethyl-silanyloxy)-cyclohexylmethyl]-9-[1-(4,6-dimethyl-pyrimidine-5-carbonyl)-4-methyl-piperidin-4-yl]-1-oxa-3,9-diaza-spiro[5.5]undecan-2-one was prepared from 40 (200 mg, 0.5 mmol) and A-9b ($R^b$=4,6-dimethyl-pyrimidin-5-yl, 170 mg, 0.38 mmol) as described in step 14 of example 1 to afford A-10 (R'=trans-4-(tert-butyl-dimethyl-silanyloxy)-cyclohexylmethyl and R"=4,6-dimethyl-pyrimidin-5-ylcarbonyl).

A solution of A-10 from the previous step (0.15 g, 0.219 mmol) in the mixture of H$_2$SO$_4$ (0.5 mL) and MeCN (2 mL) was stirred for 18 h at RT then concentrated in vacuo. The residue was dissolved in EtOAc (15 mL) and washed with sat. NaHCO$_3$. The organic layer was dried (MgSO$_4$), filtered and concentrated. The residue was purified by $SiO_2$ chromatography eluting with MeOH/DCM (1:10) to afford 100 mg of I-4 as white foam: MS [$M^+$]=570.

5-Butyl-9-[1-(4,6-dimethyl-piperidine-5-carbonyl)-4-methyl-piperidin-4-yl]-3-(cis-4-hydroxy-cyclohexylmethyl)-1-oxa-3,9-diaza-spiro[5.5]undecan-2-one (I-5) was prepared analogously starting from cis 40 to afford I-5: MS [$M^+$]=570.

I-10 can be prepared analogously except A-9b ($R^b$=4,6-dimethyl-pyrimidin-5-yl) was replaced with the corresponding amide wherein $R^b$=3-cyano-2,4-dimethyl-nicotinic acid.

EXAMPLE 6

5-Butyl-9-[1-(4,6-dimethyl-pyrimidine-5-carbonyl)-4-methyl-piperidin-4-yl]-3-(4-oxo-cyclohexylmethyl)-1-oxa-3,9-diaza-spiro[5.5]undecan-2-one (IV-2)

To a solution of I-5 (720 mg, 12.6 mmol) and DCM (50 mL) was added 4 Å molecular sieves and NMM (0.42 g, 3.6 mmol). After stirring the mixture for 10 min tetrapropylammonium perruthenate (211 mg, 0.0006 M) was added. After 1 h the solution turned black and the reaction was almost complete. The reaction mixture was diluted with DCM (50 mL), washed with solution of Na$_2$SO$_3$ (10 mL) and with brine (10 mL). The organic layer was dried (MgSO$_4$), filtered and concentrated in vacuo. The residue was purified by SiO₂ chromatography eluting with MeOH/DCM (1:10) to afford 500 mg of IV-2: MS [M⁺]=567.

EXAMPLE 7

8-Butyl-9-[1-(4,6-dimethyl-pyrinidine-5-carbonyl)-4-methyl-piperidin-4-yl]-3-(4-hydroxy-4-methyl-cyclohexylmethyl)-1-oxa-9-aza-spiro[5.5]undecan-2-one (IV-4)

To a solution of IV-2 (0.15 g, 0.26 mmol) in TF (10 mL) cooled to −30° C. was added MeMgI (0.25 mL, 0.75 mmol, 3M in Et₂O). The reaction mixture was stirred at −30° C. for 90 min then aqueous NH₄Cl (4 mL), water (2 mL) and EtOAc (10 mL) were added sequentially. The organic layer was washed with brine (5 mL), dried (MgSO₄), filtered and concentrated in vacuo. The crude residue was purified by SiO₂ chromatography eluting with DCM/MeOH/NH₄OH (450:50:0.5) to afford 47 mg of IV-4 as a white foam: MS [M⁺]=584.

Butyl-9-[1-(4,6-dimethyl-piperidine-5-carbonyl)-4-methyl-piperidin-4-yl]-3-(4-methoximino-cyclohexylmethyl)-1-oxa-9-aza-spiro[5,5]undecan-2-one (IV-11)

To a solution of methoxyamine hydrochloride (250 mg, 3.24 mmol) in 60% (v/v) aqueous MeOH (4.5 mL) was added NaOAc (0.27 g, 3.27 mmol). A solution of IV-2 (96 mg, 0.16 mmol) in 60% aqueous MeOH (5 mL) was added dropwise at RT. The mixture was stirred for 18 h, then EtOAc (5 mL) was added. The organic layer was washed with water (2×5 mL), dried (MgSO₄), filtered and concentrated in vacuo. The residue was purified by SiO₂ chromatography eluting with MeOH/DCM (1:10) to afford 48 mg of IV-11: MS M⁺=597.

8-Butyl-9-[1-(4,6-dimethyl-piperidin-5-carbonyl)-4-methyl-piperidin-4-yl]-3-(4-ethoxyimino-cyclohexylmethyl)-1-oxa-9-aza-spiro[5,5]undecan-2-one was prepared analogously except MeONH₃ Cl was replaced by EtONH₃ Cl to afford IV-12: MS M⁺=610.

EXAMPLE 8

5-Butyl-9-[1-(2,4-dimethyl-pyridine-3-carbonyl)-4-methyl-piperidin-4-yl]-3-(hexahydro-furo[2,3-b]furan-3-ylmethyl)-1-oxa-3,9-diaza-spiro[5.5]undecan-2-one (II-5)

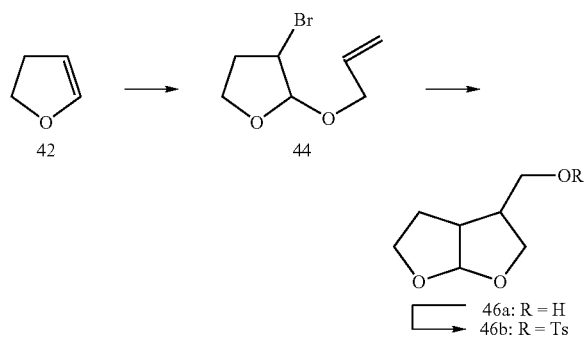

(Hexahydro-furo[2,3-b]furan-3-yl)-methanol (46a) was prepared by an N,N'-bis-(salicylidene)-ethylenediamino-cobalt (II) mediated intra-molecular radical cyclization and subsequent trapping with molecular oxygen. (T. Bamhaoud and J. Prandi, *Chem. Commun.* 1996 1229; S. Mayer et al., *Tetrahedron* 1998 54:8753)

The corresponding tosylate 46b was prepared as described in step b of example 1. The crude tosylate residue was purified by flash chromatography eluting with EtOAc/hexane (1:10) to afford 46b as a diastereomeric mixture. This mixture was separated by preparative HPLC using a Chiralpak IA column and eluting with 40% EtOH/hexane. The diastereomeric tosylates were separated cleanly: peak 1 had retention time of 33.7 min and peak 2 had retention time of 48.5 min.

To a solution of A-9b (R^b=4,6-dimethyl-pyrimidin5-yl, 91 mg, 0.2 mmol) and DMF (2 mL) was added NaH (16 mg, 0.66 mmol). After the reaction stirred for 15 min, a solution of 46b (peak 1, 100 mg, 0.33 mmol) and DMF (1 mL) was added and resulting mixture was stirred at RT for 18 h. The DMF was removed in vacuo and the residue was partitioned between EtOAc and water. The organic layer was dried (MgSO₄), filtered and concentrated. The residue was purified by SiO₂ chromatography eluting with MeOH/DCM (1:10) to afford 96 mg of II-5: MS [M⁺]=584.

The other diastereomer was prepared analogously using peak 2 from the chiral separation of the tosylates to afford II-6: MS [M⁺]=584.

EXAMPLE 9

5-Butyl-9-[1-(2,4-dimethyl-pyridine-3-carbonyl)-4-methyl-piperidin-4-yl]-3-(hexahydro-furo[2,3-b]furan-3-ylmethyl)-1-oxa-3,9-diaza-spiro[5.5]undecan-2-one (II-8)

step 10—Alkylation of A-6b (0.2 g, 0.47 mmol) with 46b (mixture of diastereomers, 0.25 g, 0.83 mmol) from example 8 using the procedure described in step 10 of example 2 afforded 180 mg of A-7 (R'=hexahydro-furo[2,3-b]furan-3-ylmethyl).

The title compound was prepared by deprotection of the product from step 10 as described in step 11 of example 2. The trifluoroacetate salt of 5-butyl-9-[1-(2,4-dimethyl-pyridine-3-carbonyl)-4-methyl-piperidin-4-yl]-3-(hexahydro-furo[2,3-b]furan-3-ylmethyl)-1-oxa-3,9-diaza-spiro[5.5]undecan-2-one (II-8) was prepared by the procedure described in step 12 of example 2 except 4,6-dimethyl-pyrimidine-5-carboxylic acid was replaced with 2,4-dimethyl nicotinic acid. The product was purified by preparative HPLC (acetonitrile-0.01M TFA).

5-{4-[5-Butyl-3-(hexahydro-furo[2,3-b]furan-3-ylmethyl)-2-oxo-1-oxa-3,9-diaza-spiro[5.5]undec-9-yl]-4-methyl-piperidine-1-carbonyl}-4,6-dimethyl-pyridine-2-carbonitrile was prepared analogously except in step 12, 2,4-dimethyl nicotinic acid was replaced by 6-cyano-2,4-dimethyl-nicotinic acid (CASRN 871492-97-6). The product was purified by SiO₂ chromatography eluting with MeOH/DCM (1:10) to afford II-7.

EXAMPLE 10

4-{5-Butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-benzonitrile (IV-3)

The title compound was prepared from A-6b as described in steps 10-12 of example 2 except in step 10, trans-toluene-4-sulfonic acid 3-methoxy-cyclohexylmethyl ester was replaced with 4-cyano-benzyl bromide. The product was purified by SiO₂ chromatography eluting with MeOH/DCM (1:10) to afford 60 mg of IV-3: MS [M⁺]=573.

EXAMPLE 11

5-Butyl-9-[1-(2,4-dimethyl-pyridine-3-carbonyl)-4-methyl-piperidin-4-yl]-3-pyrimidin-2-ylmethyl-1-oxa-3,9-diaza-spiro[5.5]undecan-2-one (IV-5)

Pyrimidin-2-ylmethyl methanesulfonate (48)—To a solution of pyrimidin-2-yl-methanol (CASRN 42839-09-8, 2 g, 1.8 mmol) and DCM (1 mL) cooled to 0° C. was added sequentially TEA (0.062 mL) and methanesulfonyl chloride (0.2 mL). The reaction mixture was stirred for 3 h then washed with aqueous NH₄Cl. The solvent was removed in vacuo and residue was purified by SiO₂ chromatography eluting with MeOH/DCM (1:20) to afford 0.2 g (58%) of 48.

The title compound was prepared by the procedure described in steps 10-12 of example 2 except in step 10, 3-methoxy-cyclohexylmethyl tosylate was replaced with 48, and in step 12, 4,6-dimethyl-pyrimidine-5-carboxylic acid was replaced with 2,4-dimethyl-nicotinic acid. The product was purified by preparative HPLC (acetonitrile-0.01M TFA) to afford IV-5 as the trifluoroacetate salt: MS [M⁺]=549.

EXAMPLE 12

5-{4-[7-Butyl-9-(4,6-dimethyl-pyrimidin-5-ylmethyl)-3,9-diaza-spiro[5.5]undec-3-yl]-4-methyl-piperidine-1-carbonyl}-4,6-dimethyl-pyridine-2-carbonitrile (IV-6)

(4,6-Dimethyl-pyrimidin-5-yl)-methanol (50)—A solution of ethyl 4,6-dimethyl-pyrimidine-5-carboxylate (CASRN 305794-79-0, 0.6 g, 3.61 mmol) and THF (10 mL) was cooled to –50° C. and DIBAL (13 mL, 0.013 mol, 1 M in toluene) was added dropwise and stirring was continued at –50° C. for 2 h. The reaction was quenched with ice/NH₄Cl and the mixture extracted with EtOAc (2×20 mL). The combined extracts were washed with brine (10 mL), dried (MgSO₄), filtered and concentrated to afford 0.33 g (67%) of 50.

2 Methanesulfonic acid, 4,6-dimethyl-pyrimidin-5-ylmethyl ester (52)—To a solution of (4,6-dimethyl-pyrimidin-5-yl)-methanol (0.33 g, 2.4 mmol) and DCM (3 mL) cooled to 0° C., was added sequentially TEA (0.18 mL) and methanesulfonyl chloride (0.3 mL). The reaction mixture was stirred for 3 h, washed with aqueous NH₄Cl and concentrated in vacuo to afford 0.38 g (78%) of the 52.

The title compound was prepared by the procedure described in steps 10-12 of example 2 except in step 10, 3-methoxy-cyclohexylmethyl tosylate was replaced with 52, and in step 12, 4,6-dimethyl-pyrimidine-5-carboxylic acid was replaced with 6-cyano-2,4-dimethyl-nicotinic acid. The crude product was purified by preparative HPLC (acetonitrile-0.01M TFA) to afford IV-6 as the trifluoroacetate salt: MS [M⁺]=586.

EXAMPLE 13

5-Butyl-9-[1-(4,6-dimethyl-pyrimidine-5-carbonyl)-4-methyl-piperidin-4-yl]-3-(3-oxa-bicyclo[3.1.0]hex-6-ylmethyl)-1-oxa-3,9-diaza-spiro[5.5]undecan-2-one (III-1)

3-Oxa-bicyclo[3.1.0]hexane-6-carboxylic acid ethyl ester (54)—A stirred suspension of 2,5-dihydrofuran (14 g, 200 mmol) and Cu(II)(acac) (1.05 g, 4 mmol) was heated at 90-100° C. and a solution of ethyl diazoacetate (27.3 g, 240 mmol) in PhH (240 mL) was added slowly over 3 h. After the addition was complete, it was cooled to RT and solvents evaporated. The residue was dissolved in petroleum ether and adsorbed on a column of neutral alumina (240 g of alumina per 10 mmol of diazoester) and eluted with 500 mL of petroleum ether and 500 mL of Et₂O. The solvent was removed and affording impure ester which was distilled at approximately 105° C. (18-19 mm Hg). The distillate was further purified by SiO₂ chromatography eluting with an EtOAc/hexane gradient (0 to 30% EtOAc) to afford 15.39 g (45.8%) of 54 (I. Reichelt and H. J. Reissig, *Chem. Ber.* 1983 116:3895).

(3-Oxa-bicyclo[3.1.0]hex-6-yl)-methanol (56)—A 1M solution of LiAlH₄ in THF (16.77 mL, 16.77 mmol) was cooled in an ice-water/acetone bath and a solution of 56 (2.62 g, 16.77 mmol) in THF (25 mL) was added slowly with stirring. The reaction was warmed to RT over 30 min and stirred for 1 h. The reaction was quenched by slow portionwise addition of 4.8 g of Na₂SO₄.10H₂O, Stirring was continued for additional 1 h after the vigorous reaction subsided. MgSO₄ was added and solids were removed by filtration, rinsed with fresh THF and solvents evaporated. The residue was purified by SiO₂ chromatography eluting with an EtOAc/hexane gradient (0 to 50% EtOAc) to afford 0.98 g (51.3%) of 56 as a colorless liquid.

step 10—To a solution of 56 (0.98 g, 8.58 mmol) and a 1:1 mixture of DCM/pyridine (10 mL) was added tosyl chloride (1.72 g, 9.01 mmol) with stirring. Stirring was continued for 18 h at RT. No tosylate observed by LCMS or TLC. The product polarity and the MS suggest the product was the pyridinium salt. The solvent was evaporated and residue used without further treatment.

A suspension of putative pyridinium salt (assumed 8.58 mmol), A-6b (2.42 g, 5.72 mmol), NaOH (0.92 g, 22.89 mmol) and tetrabutylammonium bromide (0.092 g, 0.28 mmol) in toluene (30 mL) was heated at 50° C. with stirring for 24 h. The solution was cooled and saturated aqueous NaHCO₃ was added and product extracted with DCM (4×50 mL). The combined extracts were dried (MgSO₄), filtered and concentrated. The residue was purified by SiO₂ chromatography eluting with a DCM/MB gradient (0 to 30% MB; MB=60:10:1; DCM:MeOH:NH₄OH) to afford 1.12 g (38%) of A-7 (R'=3-oxa-bicyclo[3.1.0]hex-6-ylmethyl) as a pale yellow foam: MS [M+H]⁺=520.2.

The title compound was prepared from A-7 in step 10 utilizing the procedure described in steps 11 and 12 of example 2. The crude product was purified by SiO₂ chromatography eluting with a DCM/MB gradient (0 to 30% MB; MB=60:10:1, DCM:MeOH:NH₄OH) to afford 0.249 g of II-1 as a clear foam: MS (ESI) [M+H]⁺=554.

5-(4-{(S)-5-Butyl-3-[(1R,5S,6S)-1-(3-oxa-bicyclo[3.1.0]hex-6-yl)methyl]-2-oxo-1-oxa-3,9-diaza-spiro[5.5]undec-9-yl}-4-methyl-piperidine-1-carbonyl)-4,6-dimethyl-pyridine-2-carbonitrile was prepared analogously except in step 12, 4,6-dimethyl-pyrimidine-5-carboxylic acid was replaced with 2,4-dimethyl-nicotinic acid to afford II-2: MS (ESI) [M+H]⁺=578.

(S)-5-Butyl-9-[1-(4,6-dimethyl-2-trifluoromethyl-pyrimidine-5-carbonyl)-4-methyl-piperidin-4-yl]-3-[(1R,5S,6S)-1-(3-oxa-bicyclo[3.1.0]hex-6-yl)methyl]-1-oxa-3,9-diaza-spiro[5.5]undecan-2-one (II-3) was prepared analogously except in step 12, 4,6-dimethyl-pyrimidine-5-carboxylic acid was replaced with 4,6-dimethyl-2-trifluoromethylpyrimidine-5-carboxylic acid (A. Palani et al. *Bioorg. Med. Chem. Lett.* 2003 13:709-712) to afford II-3.

EXAMPLE 14

3-(1-Acetyl-piperidin-4-ylmethyl)-5-butyl-9-[1-(4,6-dimethyl-pyrimidine-5-carbonyl)-4-methyl-piperidin-4-yl]-1-oxa-3,9-diaza-spiro[5.5]undecan-2-one (III-1)

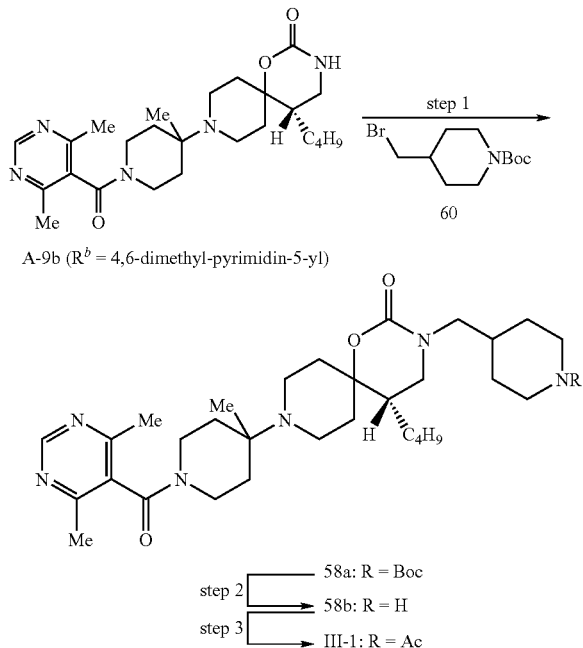

step 1—To a solution of A-9b (R$^b$=4,6-dimethyl-pyrimidin5-yl, 0.130 g, 0.3 mmol) and DMF (2.0 mL) was added NaH (0.023 g, 0.6 mmol, 60% mineral oil dispersion) and the suspension was stirred at RT for 20 min. To the resulting solution was added 60 (CASRN 158407-04-6, 0.119 g, 0.45 mmol) and the mixture was stirred overnight. LCMS indicated only partial conversion therefore additional NaH (0.023 g, 0.6 mmol) was added followed after 20 min by the addition of 60 (0.119 g, 0.45 mmol). The reaction mixture was stirred for another 24 h after which LCMS showed still some unreacted starting material. After a third addition of NaH and 60, the reaction mixture was left overnight. The flask content was quenched with water and then with saturated solution of NH$_4$Cl was added. The resulting suspension was concentrated to dryness and the residue triturated with EtOAc. After filtration and evaporation the residue was purified by SiO$_2$ chromatography eluting with a DCM/MB gradient (100% to 67% DCM, MB=DCM:MeOH:NH$_4$OH, 60:10:1) to afford 0.053 g (28%) of 58a as a foam: MS [M+H]$^+$=655.

step 2—To a solution of 58a and Et$_2$O/MeOH (3 mL, 2:1) was added 4N HCl in dioxane (1 mL) and the resulting solution was stirred overnight at 40° C. The reaction was cooled to RT and solvent evaporated.

The residue containing 58b (MS: [+H]$^+$=555) was used in the next step with further purification.

step 3—To a stirred solution of 58b (0.045 g, 0.08 mmol), DCM (1.5 mL) and pyridine (0.650 mL) was added acetic anhydride of DCM (0.046 mL, 0.49 mmol) and the resulting solution was stirred overnight at RT. The solvent was evaporated in vacuo. The residue was twice taken up in toluene and re-evaporated. The crude product was purified two preparative silica gel plate chromatographies developed with MeOH/DCM (13% MeOH) to afford 0.025 g (52%) of III-1 as a white foam: MS [M+H]$^+$ 597, [M+Na]$^+$619.

III-25 can be prepared analogously except in step 1, A-9b wherein R$^b$=4,6-dimethyl-pyrimidin-5-yl is replaced with the corresponding compound wherein R$^b$ is 3-methyl-5-trifluoromethyl-isoxazol-4-yl.

EXAMPLE 15

5-Butyl-9-[1-(4,6-dimethyl-pyrimidine-5-carbonyl)-4-methyl-piperidin-4-yl]-3-(1-isobutyryl-piperidin-4-ylmethyl)-1-oxa-3,9-diaza-spiro[5.5]undecan-2-one (III-3)

Isobutyryl chloride (0.0072 g, 0.065 mmol) was added to a solution of compound 58b (0.025 g, 0.045 mmol), DIPEA (0.016 mL, 0.09 mmol) and DCM (1 mL). The solution was stirred for 72 h at RT. The reaction was quenched with saturated NaHCO$_3$ (0.200 mL) and filtered through a CHEMELUTE® cartridge. The cartridge was washed several times with DCM and the combined eluents were concentrated to dryness. The residue was purified by SiO$_2$ chromatography eluting with a DCM/MB gradient (0 to 20% MB, MB=DCM:MeOH:NH$_4$OH, 60:10:1) to afford 0.027 g (95%) of III-3 as an off-white foam: MS [M+H]$^+$ 625.

EXAMPLE 16

5-Butyl-9-[1-(4,6-dimethyl-pyrimidine-5-carbonyl)-4-methyl-piperidin-4-yl]-3-(1-methanesulfonyl-piperidin-4-ylmethyl)-1-oxa-3,9-diaza-spiro[5.5]undecan-2-one (III-5)

The title compound was prepared utilizing a procedure analogous to example 15 except in isobutyryl chloride was replaced with methanesulfonyl chloride. The crude product was purified as described in the previous example to afford III-5 as a foam: MS [M+H]$^+$=633.

III-24 can be prepared analogously except in step 1, A-9b wherein R$^b$=4,6-dimethyl-pyrimidin-5-yl is replaced with the corresponding compound wherein R$^b$ is 3-methyl-5-trifluoromethyl-isoxazol-4-yl.

EXAMPLE 17

4-{(S)-5-Butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-piperidine-1-carboxylic acid methyl ester (III-6)

The title compound was prepared utilizing a procedure analogous to example 15 except in isobutyryl chloride was replaced with methyl chloroformate. The crude product was purified by preparative SiO$_2$ TLC developed with 1:1 DCM:MB (MB=DCM:MeOH:NH$_4$OH, 60:10:1) to afford III-6 as a white foam: MS [M+H]$^+$=613.

4-{(S)-5-Butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-piperidine-1-carboxylic acid ethyl ester (III-8) was prepared analogously except methyl chloroformate was replaced by ethyl chloroformate. The crude was purified on a preparative SiO$_2$ TLC plate developed with 10% MeOH/DCM, to afford III-8 as a foam: MS [M+H]$^+$=627 and [M+Na]$^+$=649.

III-23 can be prepared analogously except in step 1, A-9b wherein R$^b$=4,6-dimethyl-pyrimidin-5-yl is replaced with the corresponding compound wherein R$^b$ is 3-methyl-5-trifluoromethyl-isoxazol-4-yl.

EXAMPLE 18

3-(1-Acetyl-piperidin-3-ylmethyl)-5-butyl-9-[1-(4,6-dimethyl-pyrimidine-5-carbonyl)-4-methyl-piperidin-4-yl]-1-oxa-3,9-diaza-spiro[5.5]undecan-2-one (III-2)

The title compound was prepared utilizing a procedure analogous to example 14 except 4-bromomethyl-piperidine-1-carboxylic acid tert-butyl ester was replaced with 3-bromomethyl-piperidine-1-carboxylic acid tert-butyl ester (CASRN 193629-39-9) to afford III-2: MS [M+H]$^+$=597, [M+Na]$^+$=619.

3-{5-Butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-piperidine-1-carboxylic acid methyl ester (III-7) was prepared analogously except in step 3 acetic anhydride was replaced with methyl chloroformate to afford III-7 as white foam: MS [M+H]$^+$=613.

III-26 can be prepared analogously except in step 1, A-9b wherein R$^b$=4,6-dimethyl-pyrimidin-5-yl is replaced with the corresponding compound wherein R$^b$ is 3-methyl-5-trifluoromethyl-isoxazol-4-yl.

EXAMPLE 19

(S)-5-Butyl-9-[1-(4,6-dimethyl-pyrimidine-5-carbonyl)-4-methyl-piperidin-4-yl]-3-(1-oxetan-3-yl-piperidin-4-ylmethyl)-1-oxa-3,9-diaza-spiro[5.5]undecan-2-one (III-9)

To a solution of A-9b (R'=4,6-dimethyl-pyrimidin-5-yl, 0.040 g, 0.072 mmol) and MeOH (2 mL) was added HOAc (0.043 g, 0.7 mmol). After stirring at RT for 5 min, 3-ketooxetane (0.021 g, 0.29 mmol) was added to the solution followed by NaBH$_4$ (0.014 g, 0.22 mmol). The reaction mixture was stirred at RT for 16 h then the solvents were evaporated. The residue was taken in EtOAc, washed with 1N NaOH, dried (MgSO$_4$), filtered and evaporated. The residue was purified by SiO$_2$ chromatography eluting with a DCM/MB gradient on silica gel (0 to 33% MB, MB=DCM/MeOH/NH4OH, 60:10:1) to afford 0.007 g (16%) of III-9 as an off-white foam: MS [M+H]$^+$=611 and [M+Na]$^+$=633.

EXAMPLE 20

(S)-5-Butyl-3-(1-cyclopropyl-piperidin-4-ylmethyl)-9-[1-(4,6-dimethyl-pyrimidine-5-carbonyl)-4-methyl-piperidin-4-yl]-1-oxa-3,9-diaza-spiro[5.5]undecan-2-one (III-10)

To a solution of A-9b (R$^b$=4,6-dimethyl-pyrimidin-5-yl, 0.030 g, 0.054 mmol), (1-Ethoxy-cyclopropoxy)-trimethylsilane (0.014 g, 0.08 mmol) in DCM (2 mL) was added NaBH(OAc)$_3$ (0.036 g, 0.13 mmol) and the reaction mixture was stirred at RT for 16 h. The reaction was quenched with 5% NaHCO$_3$ solution and the aqueous layer was thrice extracted with DCM. The combined extracts were dried (MgSO$_4$), filtered and concentrated. The crude was purified on a preparative SiO$_2$ TLC plate developed with 1:2 DCM:MB (MB=DCM/MeOH/NH$_4$OH, 60:10:1) to afford 0.008 g (25%) of III-10 as an off-white foam: MS [M+H]$^+$=595 and [M+Na]$^+$=617.

EXAMPLE 21

(S)-5-Butyl-3-[1-(2,2-difluoro-ethyl)-piperidin-4-ylmethyl]-9-[1-(4,6-dimethyl-pyrimidine-5-carbonyl)-4-methyl-piperidin-4-yl]-1-oxa-3,9-diaza-spiro[5.5]undecan-2-one (III-11)

To a solution of A-9b (R$^b$=4,6-dimethyl-pyrimidin-5-yl, 0.100 g, 0.18 mmol), DIPEA (1.8 mmol) and MeCN (3 mL) cooled to 0° C. was added dropwise 2,2-difluoroethyl trifluoromethanesulfonate (0.058 g, 0.27 mmol). The resulting mixture was stirred for 16 h while slowly reaching RT. After quenching with saturated NaHCO$_3$ (0.200 mL) the residue was concentrated and purified by SiO$_2$ chromatography column eluting with a DCM/MB gradient (0 to 33% MB, MB=DCM/MeOH/NH4OH, 60:10:1) to afford 0.033 g (30%) of III-11 as an off-white foam: MS [M+H]$^+$=619 and [M+Na]$^+$=641.

EXAMPLE 22

3-[2-(1-Acetyl-piperidin-4-yl)-ethyl]-5-butyl-9-[1-(4,6-dimethyl-pyrimidine-5-carbonyl)-4-methyl-piperidin-4-yl]-1-oxa-3,9-diaza-spiro[5.5]undecan-2-one (III-4)

step 1—To a solution of A-9a (R$^b$=4,6-dimethyl-pyrimidin-5-yl, 0.105 g, 0.23 mmol) in DMF (3 mL) was added NaH (0.028 g, 0.71 mmol, 60% mineral oil dispersion) and the suspension was stirred at RT for 20 min. 4-[2-(Toluene-4-sulfonyloxy)-ethyl]-piperidine-1-carboxylic acid tert-butyl ester (62, CASRN 169457-73-2, 0.132 g, 0.034 mmol) was added to the solution and the mixture was stirred overnight at RT. LCMS indicated partial conversion, therefore, additional NaH (0.028 g) was added followed after 20 min by additional 62 (0.105 g) and stirring continued. After 6 h a third aliquot of NaH and 62 were added and the reaction stirred overnight. The reaction mix was quenched with water and then with saturated solution of NH$_4$Cl. The resulting suspension was concentrated to dryness and the residue triturated with EtOAc. The salts were filtered and the filtrate was concentrated in vacuo. The residue was purified by SiO$_2$ chromatography eluting with a DCM/MB gradient (0-25% MB, MB=DCM/MeOH/NH4OH, 60:10:1) to afford 0.055 g (36%) of 4-(2-{5-butyl-9-[1-(4,6-dimethyl-pyrimidine-5-carbonyl)-4-methyl-piperidin-4-yl]-2-oxo-1-oxa-3,9-diaza-spiro[5.5]undec-3-yl}-ethyl)-piperidine-1-carboxylic acid tert-butyl ester (64) as a light yellow oil: MS [M+H]$^+$=669.

step 2—TFA (0.141 g, 1.2 mmol) was added to a solution of 64 (0.055 g, 0.08 mmol) and DCM (2 mL) and the resulting solution was stirred at RT for 16 h. The solvent was removed under in vacuo and the residue was suspended twice in toluene and concentrated to dryness. The product obtained was used in the following step without further purification: MS [M+H]$^+$=669.

step 3—The title compound was prepared by the procedure described in step 3 of example 14 from the deprotected piperidine in step 2 following the procedure reported in step 3 of example 14 afford III-4: MS [M+H]⁺=611.

EXAMPLE 23

5-(4-{(S)-5-Butyl-3-[1-(2,2-difluoro-ethyl)-piperidin-4-ylmethyl]-2-oxo-1-oxa-3,9-diaza-spiro[5.5]undec-9-yl}-4-methyl-piperidine-1-carbonyl)-4,6-dimethyl-pyridine-2-carbonitrile (III-12)

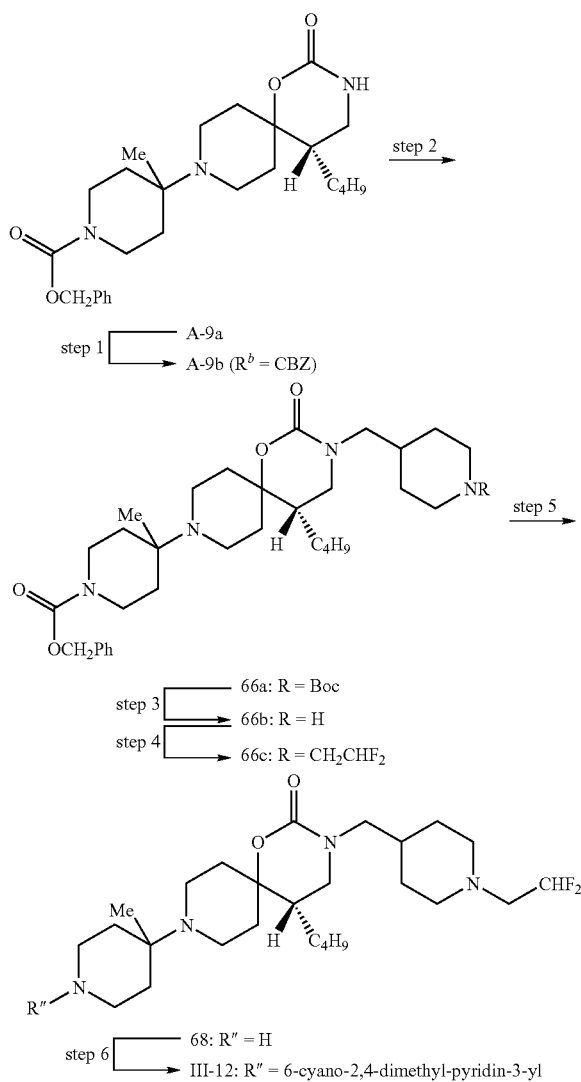

step) 1—To a suspension of A-9a (3.00 g, 6.9 mmol) and DCM (15.0 mL) at RT was added pyridine (5.59 mL, 69 mmol) and the resulting solution stirred for 30 min. The resulting solution was cooled in an ice bath and benzyl chloroformate (1.773 g, 10 mmol) was added dropwise then stirred for 1 h. The cooling bath was removed and the reaction mixture stirred overnight. The reaction mix was partitioned in DCM, 3N NaOH and the aqueous layer was twice extracted with DCM. The combined extracts were washed with brine, dried (MgSO₄), filtered and concentrated in vacuo. The crude product was purified by SiO₂ chromatography eluting with a DCM/MB gradient (0 to 10% MB, MB=DCM/MeOH/ NH₄OH, 60:10:1) to afford 1.726 g (54%) of A-9b (R$^b$=CBZ) as a light yellow oil: MS [M+H]⁺=458.

step 2—To a solution of A-9b (R$^b$=CBZ, 1.720 g, 3.76 mmol) and toluene (4.0 mL) was added 4-bromomethyl-piperidine-1-carboxylic acid tert-butyl ester (1.673 g, 6 mmol) followed by powdered NaOH (0.601 g, 15 mmol) and Bu₄NBr (0.061 g, 0.19 mmol). The resulting suspension was warmed to 50° C. and stirred at high speed for 72 h. The reaction mixture was partitioned between EtOAc/H₂O and the aqueous layer was back extracted twice with EtOAc. The combined extracts were washed with brine, dried (MgSO₄), filtered and concentrated in vacuo. The crude product obtained was purified by SiO₂ chromatography elution with a DCM/MeOH gradient (0 to 5% MeOH) to afford 2.006 g (82%) of 66a as a white foam: MS [M+H]⁺=655.

step 3—To a solution of 66a (2.00 g, 3.1 mmol) and DCM (5 mL) was added TFA (3.53 mL, 46 mmol) and the reaction was stirred for 16 h at RT. The solution was concentrated almost to dryness and the remaining solvent was removed by co-evaporation with toluene. The residue was partitioned between 5M NaOH and DCM. The layers were separated and the aqueous layer twice extracted with DCM. The combined organic phases were washed with brine, dried (MgSO₄), filtered, and concentrated to afford 66b (1.740 g, 100% yield) as a light yellow syrup which was without further purification: MS [M+H]⁺=555.

step 4—The difluoroethylamine 66c was prepared from 66b and 2,2-difluoroethyl trifluoromethanesulfonate as described in example 21 to afford 66c: MS [M+H]⁺=619.

step 5—To a solution of 66c (0.630 g, 1 mmol) and EtOH (50 mL) in a flask flushed with argon was added Pearlman's catalyst (20% Pd(OH)₂/C, 0.100 g). The flask was flushed again with argon then with hydrogen. A hydrogen balloon connected to a syringe with a needle was inserted through a septum so that hydrogen bubbling through the solution. Reaction was stirred for 16 h. The catalyst was removed by filtration and the filtrate was concentrated to dryness. The crude obtained was purified SiO₂ chromatography eluting with a DCM/MB gradient (0 to 50% MB, MB=DCM/MeOH/ NH₄OH, 60:10:1) to afford 0.415 g (84%) of 68 as a light yellow foam: MS [+H]⁺=485.

step 6—A solution of 68 and DMF, 6-cyano-2,4-dimethyl-nicotinic acid, DIPEA and HATU were stirred overnight at RT. The solvent was removed in vacuo and the residue partitioned between DCM and 3N NaOH. The aqueous layer was back extracted with DCM and the combined organics were dried (MgSO₄), filtered and evaporated. The product was purified by SiO₂ chromatography eluting with a DCM/MB gradient (MB=DCM/MeOH/NH4OH, 60:10:1) to afford III-12: MS [M+H]⁺=643.

EXAMPLE 24

(S)-5-Butyl-9-[1-(4,6-dimethyl-piperidine-5-carbonyl)-4-methyl-piperidin-4-yl]-3-[2-(tetrahydro-pyran-4-yl)-ethyl]-1-oxa-3,9-diaza-spiro[5.5]undecan-2-one (IV-10)

step 1-toluene-4-sulfonic acid 2-(tetrahydro-pyran-4-yl)-ethyl ester (70)—p-Toluenesulfonyl chloride (2.998 g, 16 mmol) was added to a solution of 2-(tetrahydro-pyran-4-yl) ethanol (CASRN 4677-18-3, 1.706 g, 13 mmol), pyridine (1.16 mL, 14 mmol) and DCM (10 mL). The resulting mixture was stirred at RT for 72 h. The solution was partitioned between EtOAc and saturated NH₄Cl. The aqueous layer was back extracted twice with EtOAc. The combined organic phases were dried (MgSO$_4$), filtered and concentrated in vacuo to afford 70 as colorless oil.

step 2—4-{(S)-5-Butyl-2-oxo-3-[2-(tetrahydro-pyran-4-yl)-ethyl]-1-oxa-3,9-diaza-spiro[5.5]undec-9-yl}-4-methyl-piperidine-1-carboxylic acid tert-butyl ester (72) was prepared from A-6b and 70 by the procedure described in step 1 of example 22 to afford 72: MS [M+H]$^+$=536.

step 3—To a solution of 72 (0.529 g, 1 mmol) and toluene (5 mL) was added 3M HCl (0.530 mL) and the reaction mix was warmed to 45° C. and stirred at high speed for 1.5 h. The reaction flask warmed RT and the aqueous layer was separated and adjusted to pH 14 with 40% NaOH then thrice extracted with 2-methyl tetrahydrofuran and the combined organics were dried (MgSO$_4$), filtered and concentrated to afford 0.307 g (71% yield) of 74 as a light yellow oil which was used in the next step without additional purification.

step 4—To a solution of 74 (0.307 g, 0.7 mmol) and 4,6-dimethyl-pyrimidine-5-carboxylic acid (0.118 g, 0.78 mmol) in 2-methyl-tetrahydrofuran (3.5 mL, MeTHF) was added sequentially HOBt (0.105 g, 0.78 mmol), EDCI (0.149 g, 0.78 mmol) and DIPEA (0.250 mL, 1.4 mmol). The reaction was warmed to 50° C. and stirred for 16 h. The reaction was quenched by addition of 3N NaOH (1.3 mL). The organic layer was isolated and the aqueous layer was back extracted twice with MeTHF (1 mL). The combined organics were washed with brine, dried (MgSO$_4$), filtered and concentrated in vacuo. The crude product was purified by SiO$_2$ chromatography eluting with a DCM/MB gradient (0 to 33% MB, MB=DCM/MeOH/NH$_4$OH, 60:10:1) to afford 0.233 g (58%) of IV-10 as a white foam: MS [M+H]$^+$=570.

EXAMPLE 25

(S)-5-Butyl-3-(4,4-difluoro-cyclohexyl)-9-[1-(4,6-dimethyl-pyrimidine-5-carbonyl)-4-methyl-piperidin-4-yl]-1-oxa-3,9-diaza-spiro[5.5]undecan-2-one (IV-7)

step 1—To a solution of 1,4-cyclohexanediol (20.0 g, 172 mmol) and pyridine (100 mL) cooled to 0° C. was added dropwise over 2 h a solution of 32.0 g (168 mmol)$_p$-toluene-sulfonyl chloride in CHCl$_3$ (100 mL). After the addition was complete the reaction mixture was stirred at RT for 17 h. The solvent was evaporated in vacuo and the residue was taken up in refluxing toluene and petroleum ether was added until the solution became cloudy. The mixture was cooled and the supernatant was decanted. The remaining solid was dissolved in DCM and vacuum filtered through a pad of SiO$_2$. The filter cake was washed with a mixture of DCM/MeOH (95:5). The dark golden oil was dried under vacuum to afford 35.6 g (78%) of toluene-4-sulfonic acid 4-hydroxy-cyclohexyl ester (76) contaminated with a small amount of bis-tosylate: $^1$H NMR (CDCl$_3$, 300 MHz): δ 7.79 (dd, 2H), 7.73 (dd, 2H), 4.64-4.48 (m, 1H), 3.75-3.69 (m, 1H), 2.45 (s, 3H), 1.95-1.83 (m, 3H), 1.70-1.26 (m, 6H).

step 2—To a solution of 76 (2.23 g, 8.22 mmol) and CHCl$_3$ (30 mL) was added PCC (1.77 g, 8.22 mmol) and CHCl$_3$ (20 mL). One drop of HOAc was added and the mixture was stirred at RT for 2.5 days. An additional 1.77 g (8.22 mmol) of PCC was added and stirring continued at RT for an additional 6 h. The reaction was diluted with Et$_2$O and filtered through a bed of SiO$_2$. The cake was washed with Et$_2$O and the filtrate was passed through a second plug of SiO$_2$ while washing the cake with Et$_2$O. The filtrate was stripped in vacuo and the crude material was purified by SiO$_2$ chromatography eluting with a DCM/MeOH gradient (0 to 4% MeOH). The recovered material was re-purified by SiO$_2$ chromatography eluting with a gradient of hexane/acetone (15 to 25% acetone) to afford 1.32 g (58%) of toluene-4-sulfonic acid 4-oxo-cyclohexyl ester (78) as a colorless oil: $^1$H NMR (CDCl$_3$, 300 MHz): δ 7.83 (d, 2H), 7.37 (d, 2H), 4.92-4.86 (m, 1H), 2.78-2.53 (m, 2H), 2.46 (s, 3H), 2.34-2.13 (m, 4H), 2.03-1.83 (m, 2H).

step 3—To a solution of 78 (200 mg, 0.75 mmol) and DCM (7 mL) cooled to 0° C. was added DAST (363 mg, 2.25 mmol). The cooling bath was removed and the mixture was stirred at RT for 3 h. The reaction was quenched with water and diluted with DCM. The DCM phase was washed successively with 1M HCl, saturated NaHCO$_3$, and brine, dried (Na$_2$SO$_4$) and concentrated in vacuo. The crude material was purified by SiO$_2$ chromatography eluting with hexane/EtOAc (75:25) to afford. The white solid was dried to give 135 mg (62%) of toluene-4-sulfonic acid 4,4-difluoro-cyclohexyl ester (80): $^1$H NMR (CDCl$_3$, 300 MHz): δ 7.80 (d, 2H), 7.35 (d, 2H), 4.77-4.69 (m, 1H), 2.46 (s, 3H), 2.39-1.76 (m, 8H).

step 4—To a solution of A-9b (R$^b$=4,6-dimethylpyrimdin-yl, 649 mg, 1.42 mmol) and DMF (7 mL) was added NaH (284 mg, 7.10 mmol, 60% dispersion in mineral oil). The mixture was stirred at RT under argon for 5 min, then a solution of 80 (495 mg, 1.70 mmol) and DMF (6 mL) was added. The reaction mixture was heated at 160° C. for 6 min under microwave irradiation. Additional aliquots of NaH (142 mg, 3.55 mmol) and 80 (55 mg, 0.19 mmol) were added and the mixture was heated at 160° C. for 10 min under microwave irradiation. The reaction mixture was cooled and diluted with water and EtOAc and stirred vigorously for 10 min. The mixture was filtered through CELITE® and the filter cake washed with EtOAc. The aqueous phase was extracted twice with EtOAc and the combined organic extracts were washed with water, 50% brine and brine, dried (Na$_2$SO$_4$), and evaporated to afford a golden oil. The crude product was purified by SiO$_2$ chromatography eluting with a DCM/MeOH gradient (4 to 7% MeOH) to afford 60 mg (7%) of IV-7 as a light yellow powder: MS (ESI) [M+H]$^+$=576.

EXAMPLE 26

(S)-5-Butyl-9-[1-(4,6-dimethyl-pyrimidine-5-carbonyl)-4-methyl-piperidin-4-yl]-3-pyridin-2-yl-1-oxa-3,9-diaza-spiro[5.5]undecan-2-one (IV-8)

step 1—A solution of Pd$_2$(DBA)$_3$ (114 mg, 0.125 mmol), 9,9-dimethyl-4,5-bis(diphenylphosphino)xanthene (14 mg, 0.05 mmol) and toluene (1 mL) was stirred under argon for 20 min. To this solution was added A-6b (91 mg, 0.95 mmol), NaO-tert-Bu (91 mg, 0.95 mmol), 2-bromopyridine (48 µL, 0.5 mmol) with 1 mL toluene and the reaction was heated to reflux under argon. After 24 h the reaction was cooled, quenched with water and diluted with EtOAc. The mixture was filtered through CELITE® and the phases were separated. The organic layer was washed with water and brine, dried (Na$_2$SO$_4$), filtered and evaporated to afford a brown syrup. The crude product was purified by SiO$_2$ chromatography eluting with a DCM/MeOH (0 to 8% MeOH) to afford 250 mg (100%) of 4-(5-butyl-2-oxo-3-pyridin-2-yl-1-oxa-3,9-diaza-spiro[5.5]undec-9-yl)-4-methyl-piperidine-1-carboxylic acid tert-butyl ester (82) as a brown glass: MS (ESI) [M+H]$^+$=501.

step 2—A solution of 82 (250 mg, 0.5 mmol), DCM (10 mL) and TFA (1 mL) was stirred at RT for h. The solvent was evaporated in vacuo and the residue partitioned between 5M NaOH and EtOAc. The phases were separated and the aqueous extracted four times with EtOAc. The combined organic phases were washed with water, 50% brine and brine, dried (Na$_2$SO$_4$) and evaporated to afford 64 mg of the deprotected piperidine 84 as a thick brown syrup. To a solution of 84 (64 mg, 0.16 mmol), 4,6-dimethyl-pyrimidine-5-carboxylic acid (29 mg, 0.19 mmol), HOBt (28 mg, 0.21 mmol), EDCI (40 mg, 0.21 mmol) in DMF (2 mL) was added DIPEA (84 µL, 0.48 mmol). The reaction was stirred at RT for 2.5 d. The reaction was quenched with water and diluted with EtOAc. The phases were separated and the aqueous extracted twice with EtOAc. The combined organic extracts were washed twice with water and brine, dried ($Na_2SO_4$) and evaporated. The crude material was purified by $SiO_2$ chromatography eluting with DCM/MeOH (95:5) to afford 57 mg (67%) of IV-8 as a white foam: MS (ESI) $(M+H)^+$=535, $[M+Na]^+$=557.

5-[4-((S)-5-Butyl-2-oxo-3-pyridin-2-yl-1-oxa-3,9-diaza-spiro[5.5]undec-9-yl)-4-methyl-piperidine-1-carbonyl]-4,6-dimethyl-pyridine-2-carbonitrile (IV-9) was prepared analogously except in step 2,4,6-dimethyl-pyrimidine-5-carboxylic acid was replaced with 6-cyano-2,4-dimethylnicotinic acid. The crude material was purified by $SiO_2$ chromatography eluting with a DCM/MeOH (0 to 7% MeOH) to afford 97 mg (62%) of IV-9 as an off-white solid: MS (ESI) $[M+H]^+$=559.

EXAMPLE 27

(1R,5S,6R)-6-{(S)-5-Butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-3-aza-bicyclo[3.1.0]hexane-3-carboxylic acid ethyl ester (III-16)

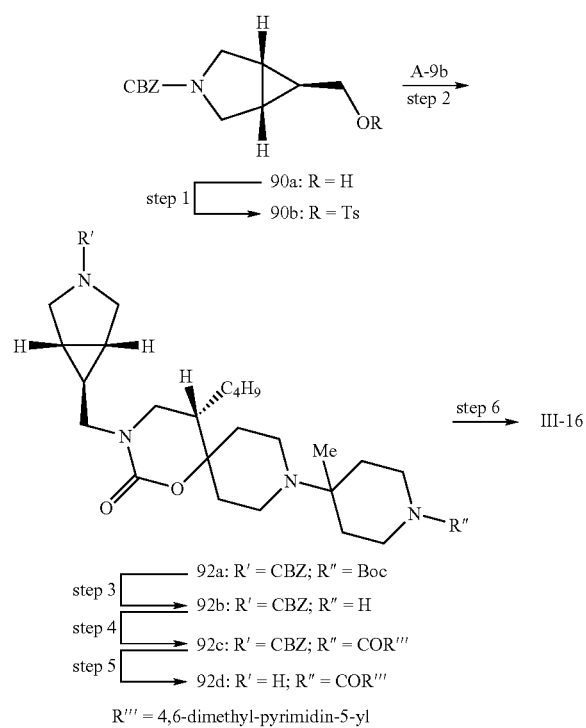

3-Aza-bicyclo[3.1.0]hexane-3-carboxylic acid benzyl ester (90a) was prepared following the procedures described by K. E. Brightly et al. EP 0 413 456 B1.

step 1-p-Toluenesulfonyl chloride (1.378 g, 7.23 mmol) was added to a solution of 90a (1.49 g, 6.02 mmol) and DCM (30 mL) and TEA (1.26 mL, 9.0 mmol) of TEA cooled to 0° C. The resulting mixture was stirred for 20 min at 0° C. and then allowed to warm to RT and stirred overnight. The solution was partitioned between DCM and saturated solution of $NH_4Cl$ and the aqueous layer was extracted twice with DCM. The combined organics extracts were washed with brine, dried ($MgSO_4$), filtered and evaporated. The resulting light yellow oil was purified $SiO_2$ chromatography eluting with an EtOAc/hexane gradient (0 to 30% EtOAc) to afford 0.556 g (23%) of 90b as a colorless oil.

step 2—To a solution of A-9b ($R^b$=tert-butoxy, 0.25 g, 0.59 mmol) and toluene (1.5 mL) was added sequentially powdered NaOH (0.094 g, 2.361 mmol) $NBu_4Br$ (0.01 g, 0.03 mmol) and a solution of 90b (0.38 g, 0.944 mmol) and toluene (1 mL). The reaction mix was heated to 55° C. for 3 h, cooled to RT, quenched with $H_2O$ and partitioned between $H_2O$ and EtOAc. The aqueous layer was extracted with EtOAc and the combined extracts were dried ($Na_2SO_4$), filtered and evaporated. The residue was purified by $SiO_2$ chromatography eluting with a MeOH/DCM gradient (0 to 3% MeOH) to afford 0.328 g (85%) of 92a as a white foam.

step 3—The Boc group was removed by treatment with 4N HCl in dioxane as described in step 2 of example 14 to afford 92b.

step 4—Acylation of 92b with 4,6-dimethyl-pyrimidine-5-carboxylic acid was carried out as described in step 13 of example 1 to afford 92c.

step 5—A flask was charged with 92c (0.3 g, 0.437 mmol), and $Pd(OH)_2$ (0.06 g, 20% wt) and EtOH (5 mL) and evacuated and flushed twice with $N_2$ and then three times with $H_2$. The reaction mix was stirred under 1 atm of $H_2$, overnight at RT. The palladium was filtered through a bed of CELITE and the filtrate was evaporated and dried under high vacuum to afford 0.223 g (92%) of 92d as a pale brown foam.

step 6—To a solution of 92d (0.05 g, 0.09 mmol) and DIPEA (0.03 mL, 0.181 mmol) and DCM (1 mL) was added methyl chloroformate (0.01 mL, 0.136 mmol) and the resulting mixture was stirred at RT for h. The reaction mixture was partitioned between DCM and aqueous $NaHCO_3$ and the aqueous layer was twice extracted with DCM. The combined extracts were dried ($Na_2SO_4$), filtered and evaporated. The residue was purified by $SiO_2$ chromatography eluting with a MeOH/DCM gradient (0 to 5% MeOH) to afford 0.027 g (49%) of III-16 as a pale yellow foam: ms $[M+H]^+$ 611.

III-17 and III-18 were prepared analogously except in step 6, methyl chloroformate was replaced with ethyl chloroformate and iso-propyl chloroformate respectively. III-19 was prepared analogously except the acylation in step 6 was replaced by alkylation of 92d with 2,2-difluoroethyl triflate as described in example 21. III-19 and III-14 were prepared analogously using ethyl chloroformate and acetic anhydride as the acylating agent in step 6 and replacing 4,6-dimethyl-pyrimidine-5-carboxylic acid with 3-methyl-5-(trifluoromethyl)-isoxazole-4-carboxylic acid in step 4.

EXAMPLE 28

(S)-3-{(S)-5-Butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-pyrrolidine-1-carboxylic acid methyl ester (III-14)

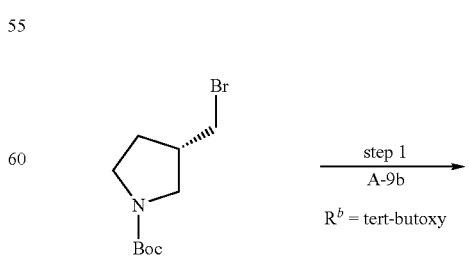

R' = 4,6-dimethyl-pyrimindin-5-yl

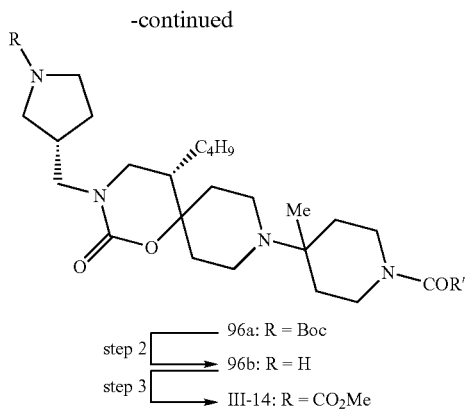

step 2 ── 96a: R = Boc
       → 96b: R = H
step 3
       → III-14: R = CO₂Me

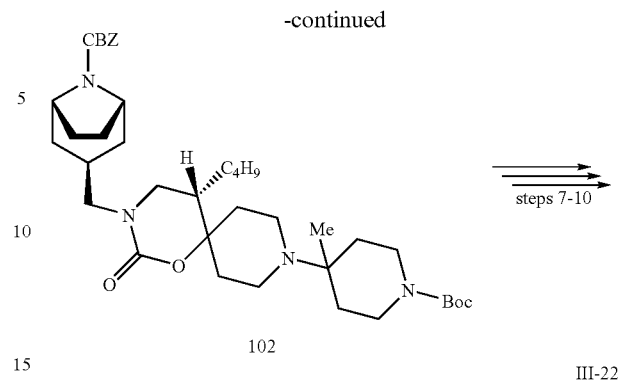

III-22

(S)-1-tert-Butoxycarbonylpyrrolidine-3-methanol [CASRN 199174-24-8] and (R)-1-tert-butoxycarbonylpyrrolidine-3-methanol [CASRN 138108-72-2] can be converted to the corresponding bromide by the procedure of M. O. Polla et al. *Bioorg. Med. Chem. Lett.* 2004 12:1151-1175.

step 1—Alkylation of A-9b ($R^b$=tert-butoxy, 0.25 g, 0.59 mmol) by 94 was carried out using the procedure described in step 2 of example 27 to afford 96a.

step 2—The Boc group of 96a was removed by treatment with 4N HCl in dioxane as described in step of example 14 to afford 96b.

step 3—The amino group of 96b was acylated with methyl chloroformate as described in step 6 of example 27 to afford III-14: ms [M+H]⁺ 599, [M+Na]⁺ 619.

III-13 was prepared analogously except ethyl chloroformate was used in place of methyl chloroformate in step 3. III-15 was prepared analogously except the acylation in step 3 was replaced by alkylation of 96b with 2,2-difluoroethyl triflate as described in example 21.

EXAMPLE 29

(1S,3R,5R)-3-{(S)-5-Butyl-9-[1-(4,6-dimethyl-piperidine-5-carbonyl)-4-methyl-piperidin-4-yl]-2-oxo-1-oxa-3,9-diaza-spiro[5.5]undec-3-ylmethyl}-8-azabicyclo[3.2.1]octane-8-carboxylic acid methyl ester (III-22)

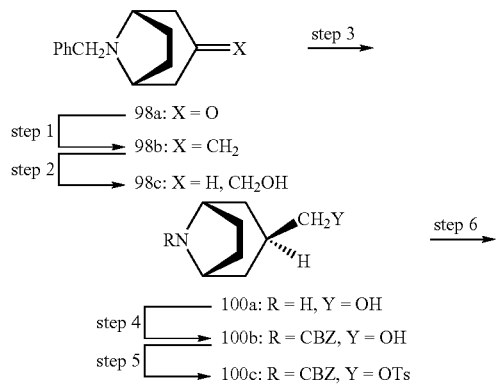

step 1 ── 98a: X = O
       → 98b: X = CH₂
step 2
       → 98c: X = H, CH₂OH step 4 ── 100a: R = H, Y = OH
       → 100b: R = CBZ, Y = OH
step 5
       → 100c: R = CBZ, Y = OTs step 1—Methyltriphenylphosphonium bromide/sodium amide (2.4 mmol/g, 0.261 g, 0.627 mmol, Aldrich) was suspended in THF (50 mL) and stirred at RT for ca. 30 min. (1R,5S)-8-benzyl-8-aza-bicyclo[3.2.1]octan-3-one (98a) (5 g, 23.22 mmol) was dissolved in THF (50 mL) and added slowly to the reaction flask and the resulting suspension was stirred at RT overnight. The reaction mix was filtered through CELITE and the filter cake was washed with EtOAc. The filtrate was evaporated and dried under high vacuum. The remaining brown oil was triturated in hexanes and filtered giving a sticky solid, which was taken up and triturated twice more in hexanes. The filtrate was evaporated and dried under high vacuum leaving 4.0 g (81%) of 98b as a pale yellow liquid.

step 2-A solution of 98b (0.155 g, 0.727 mmol) and THF (1.5 μL) was added to an ice-cold solution of disiamylborane and THF (1M in THF, 3.63 mL, 3.63 mmol). The reaction mix was then allowed to warm to RT and stirred for 3 h. The colorless clear solution was cooled to 0° C. degrees and NaOH (aqueous 3M, 0.73 mL, 2.18 mmol) was added followed by H₂O₂ solution (aqueous 30 wt %, 0.35 mL, 3.633 mmol). The mixture became biphasic and was allowed to warm up to RT. After ca. 30 min the reaction mix was partitioned between Et₂O and H₂O and the aqueous layer was extracted with Et₂O. The combined extracts were washed with brine, dried (Na₂SO₄), filtered and concentrated. The residue was purified by SiO₂ chromatography eluting with a gradient of DCM and a solution of DCM/MeOH/NH₄OH (60/10/1) (100 to 60% DCM) to afford 0.110 g (65%) of 98c as a colorless oil.

step 3—A flask was charged with EtOH (50 mL), 98c (4.71 g, 20.36 mmol) and Pd(OH)₂ (0.95 g, 20 wt %). The flask was evacuated and flushed twice with N₂ and flushed afterwards three times with H₂. The reaction mixture was stirred at RT for 48 h under 1 atm of H₂. The palladium catalyst was removed by filtration through a bed of CELITE and the filtrate was evaporated and dried under high vacuum to afford 2.98 g (100%) of 100a as a white solid.

step 4—TEA (4.4 mL, 31.65 mmol) was added to a suspension of 100a (2.98 g, 21.103 mmol) in MeCN (70 mL) and the reaction flask was cooled to 0° C. Benzyl chloroformate (4.8 mL, 31.65 mmol) was added to the solution and the reaction mix was allowed to warm up to RT and stirred for 2 h. The residue was partitioned between water and DCM and the aqueous layer was back extracted twice with DCM. The combined extract were dried (Na₂SO₄), filtered and evaporated. The remaining orange oil was purified by SiO₂ chromatography eluting with a MeOH/DCM gradient (0 to 4% MeOH) to afford 3.57 g (61%) of 100b as a light yellow oil.

step 5—Tosylation of 100b was carried out as described in step 1 of example 27 to afford 100c.

Alkylation of A-9b ($R^b$=tert-butoxy) with 100c (step 6) was carried out as described in step 2 of example 27. Removal of the Boc protecting group (step 7) was carried out with 4N HCl in dioxane as described in step 2 of example 14. Acylation (step 8) of the resulting secondary amine with 2,6-dimethyl-pyrimidine-5-carboxylic acid was carried out as described in step 13 of example 1. Removal of the CBZ protecting group (step 9) and acylation of the resulting amine with methyl chloroformate (step 10) were carried out as described in steps 5 and 6 of example 27 to afford III-22: ms [M+H]$^+$ 639.

The completion of the synthesis was carried out as described previously. After acid-catalyzed removal of the Boc group the piperidine nitrogen was acylated with 4,6-dimethyl-pyrimidine-5-carboxylic acid then hydrogenolytic removal of the CBZ protecting group and acylation of the amine with methyl chloroformate.

EXAMPLE 30

(S)-5-Butyl-9-[1-(4,6-dimethyl-piperidine-5-carbonyl)-4-methyl-piperidin-4-yl]-3-(tetrahydro-pyran-4-yl)-1-oxa-3,9-diaza-spiro[5.5]undecan-2-one (IV-13)

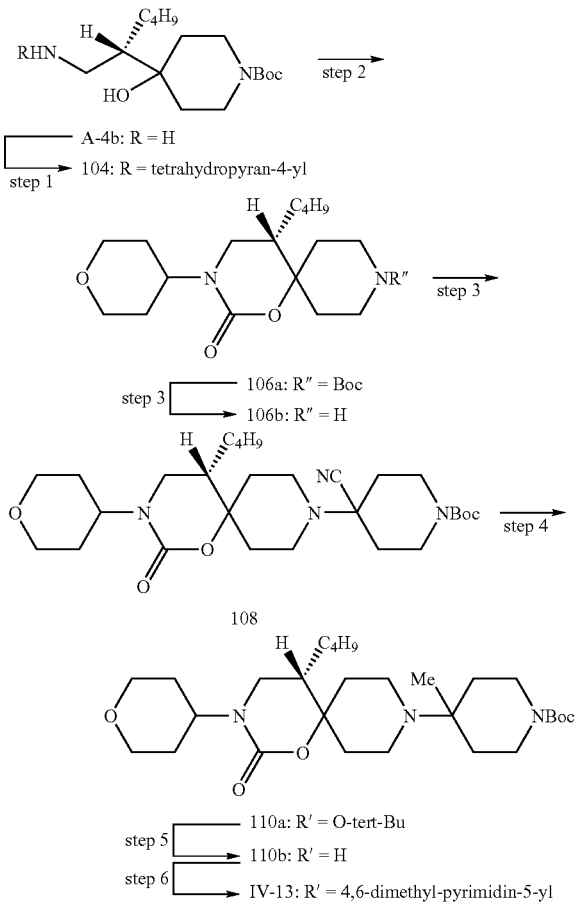

step 1—A solution of A-4b (3.33 mmol), 4-ketotetrahydropyran (349 mg, 3.49 mmol), titanium tetraisopropoxide (1.33 g, 4.66 mmol) in DCE (22 mL) was stirred at RT for 17 h then NaBH$_4$ (1.06 g, 5.00 mmol) was added. The reaction mixture was stirred vigorously for 4.5 h then quenched with 1M NaOH. The mixture was partitioned between water and DCM, stirred vigorously for 15 min and filtered through CELITE. The cake was washed with DCM and the phases were separated. The aqueous was twice extracted with DCM and the combined organic extracts were dried (Na$_2$SO$_4$), filtered and evaporated to a yellow oil. The residue was dried in vacuo to afford 800 mg (63%) of 104 which was used without further purification: ms (ESI): m/z 385 (M+H).

step 2—To a solution of 104 (800 mg, 2.08 mmol) and THF (25 mL) was added a solution of carbonyl diimidazole (506 mg, 3.12 mmol) and THF (10 mL). The mixture was stirred at RT for 23 h. The reaction was quenched with 1M HCl and concentrated in vacuo. The oily aqueous phase was extracted twice with EtOAc. The combined extracts were washed successively with saturated NaHCO$_3$, water and brine, dried (Na$_2$SO$_4$), filtered and evaporated. The residue was purified by SiO$_2$ chromatography eluting with a MeOH/DCM gradient (0 to 10% MeOH) and the recovered oil in vacuo to afford 164 mg (19%) of 106a: MS (ESI): m/z 411 (M+H).

step 3—To a solution of 106a (164 mg, 0.40 mmol) and DCM (5 mL) was added TFA (1 mL) and the reaction was stirred at RT for 17 h. The solvent was evaporated in vacuo and the residue partitioned between 5M KOH and EtOAc. The phases were separated and the aqueous layer extracted two times with EtOAc. The combined organic extracts were washed with brine, dried (Na$_2$SO$_4$), filtered and evaporated. The yellow syrup was dried under in vacuo to afford 100 mg (81%) of 106b. To a solution of the crude material in DCE (3 mL) was added sequentially a solution of N—BOC 4-piperidone (68 mg, 0.34 mmol) and DCE (2 mL) and titanium tetraisopropoxide (128 mg, 0.45 mmol). The reaction was stirred at RT for 16 h after which diethylaluminumcyanide (480 µl, 0.48 mmol, 1M in toluene) was added. The reaction was stirred at RT for 3.5 h then quenched with 1M NaOH and partitioned between CH$_2$Cl$_2$ and H$_2$O. The mixture was filtered through CELITE and the filter cake washed with DCM. The phases were separated and the organic phase was dried (Na$_2$SO$_4$), filtered and evaporated. The solvent was stripped in vacuo to afford 108 as a clear syrup which was used without further purification. MS (ESI): m/z 520 (M+H).

step 4—To a solution of 108 (166 mg, 0.32 mmol) and THF (10 mL) was added methylmagnesium bromide (533 µL, 1.60 mmol, 3M in ether) and the reaction was stirred at RT for 4 h. An additional aliquot of MeMgBr (533 µl) was added and the reaction was stirred for 1 h. A second aliquot of MeMgBr (267 µL, 0.80 mmol) was added and the reaction was stirred at RT for 17 h more. The reaction was quenched with water and diluted with EtOAc. Saturated NH$_4$Cl was added until the phases were clear (the aqueous phase was still basic). The phases were separated and the aqueous layer extracted with EtOAc. Combined organic extracts were washed with brine, dried (Na$_2$SO$_4$), filtered and evaporated. The crude material was purified by SiO$_2$ chromatography eluting with a gradient of MeOH/DCM (0 to 10% MeOH) to afford 51 mg (31%) of 110a as a clear glass: MS (ESI): m/z 509 (M+H).

steps 5 & 6—To a solution of 110a (51 mg, 0.10 mmol) and DCM (5 mL) was added TFA (1 mL) and the reaction was stirred at RT for 6 h. The solvent was evaporated in vacuo and the residue partitioned between 5M KOH and EtOAc. The phases were separated and the aqueous extracted two times with EtOAc. The combined organic extracts were washed with water and brine, dried (Na$_2$SO$_4$), filtered and evaporated to afford 110b. To a solution of 110b (17 mg, 0.04 mmol), 4,6-dimethylpiperidine-5 carboxylic acid (7 mg, 0.044 mmol), HOBt (7 mg, 0.052 mmol) and DMF (0.5 mL) was added EDCI (10 mg, 0.052 mmol) followed by DIPEA (21 μl, 0.12 mmol). The reaction was stirred at RT for 18 h. The reaction was quenched with water and diluted with EtOAc. The phases were separated and the aqueous extracted two times with EtOAc. The combined EtOAc extracts were dried (Na$_2$SO$_4$), filtered and evaporated. The crude material was purified by Prep HPLC to give 8.1 mg (37%) of IV-13 as a white solid: MS (ESI), m/z 542 (M+H).

EXAMPLE 31

5-{4-[(S)-5-Butyl-3-(2,2-difluoroethyl)-2-oxo-1-oxa-3,9-diazaspiro[5.5]undec-9-yl]-4-methylpiperidine-1-carbonyl}-4,6-dimethylpyridine-2-carbonitrile (III-26)

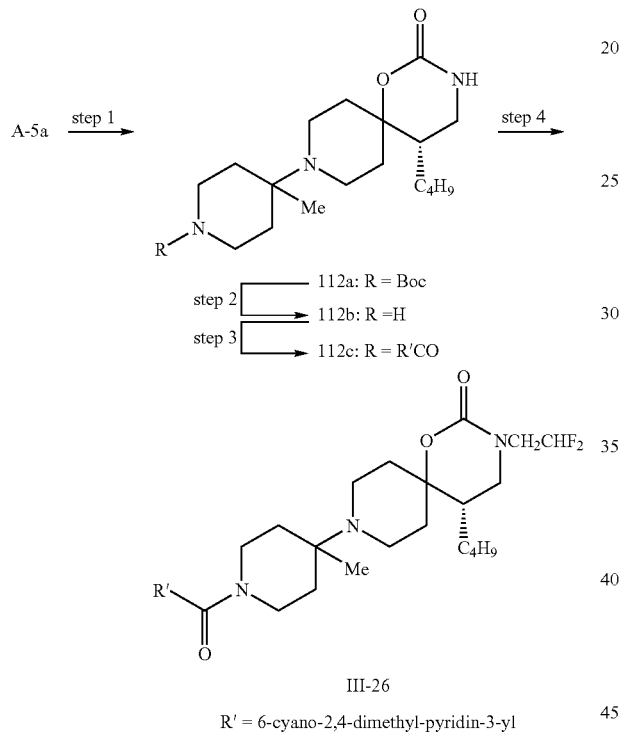

R' = 6-cyano-2,4-dimethyl-pyridin-3-yl

The synthesis of A-5a was described by S. D. Gabriel and D. Rotstein in US Pat. Publication 2005/0176703. A-5a was converted to 112b by removal of the Boc group, reductive amination with N-Boc-4-piperidone, introduction of the 4-methyl and Boc deprotection essentially as described in steps 3-5 of example 30.

step 3—To a solution of 112b (672 mg, 2.08 mmol), 4-cyano-2,6-dimethyl-3-pyridinyl carboxylic acid (366 mg, 2.08 mmol), HOBt (365 mg, 2.70 mmol) HOBT and DMF (10 mL) was added EDCI (518 mg, 2.70 mmol) followed by DIPEA (1.1 mL, 6.24 mmol). The reaction was stirred at RT for 50 h. The reaction was quenched with water and diluted with EtOAc. The phases were separated and the aqueous extracted two times with DCM. The combined organic phase was dried (Na$_2$SO$_4$), filtered and evaporated. The crude material was purified by Prep HPLC to afford 8.1 mg (37%) of 112c as a white solid: MS (ESI) m/z 542 (M+H).

step 4—To a solution of 112c (33 mg, 0.069 mmol) and DMF (1 μL) was added NaH (14 mg, 0.34 mmol, 60% mineral oil dispersion). The mixture was stirred at RT under argon for 15 min then a solution of 1,1-difluoroethyl triflate (44 mg, 0.21 mmol) in DMF (0.5 mL) was added. The reaction was stirred at RT for h. The reaction was quenched with water and diluted with EtOAc. The phases were separated and the aqueous extracted with EtOAc. The combined extracts were dried (Na$_2$SO$_4$), filtered and evaporated. The crude material was purified by SiO$_2$ chromatography eluting with a MeOH/DCM gradient 0 to 2% MeOH) followed by Prep HPLC to afford 8.0 mg (21%) of III-26 as a white solid: MS (ESI) m/z 546 (M+H).

EXAMPLE 32

5-(S)-Butyl-9-[1-(4,6-dimethyl-pyrimidine-5-carbonyl)-4-methyl-piperidin-4-yl]-3-[1,4]dioxin-2-(R)-ylmethyl-1-oxa-3,9-diaza-spiro[5.5]undecan-2-one (III-9)

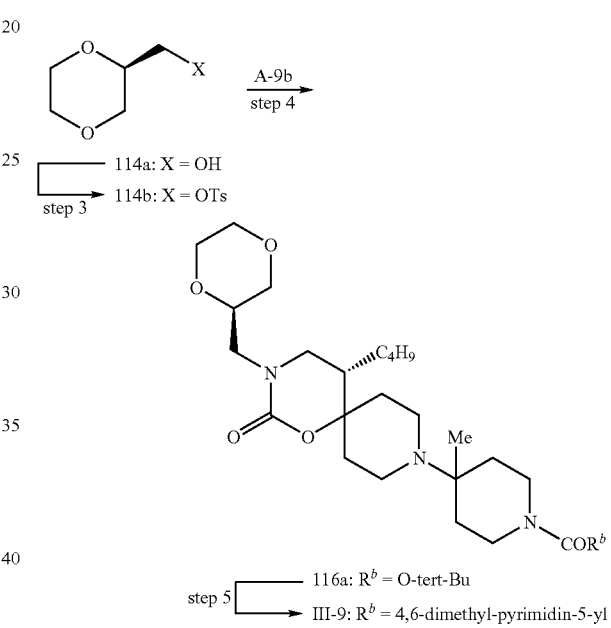

step 1—To a solution of R-(−)-epichlorohydrin (7 mL, 89.27 mmol) and DCE (280 mL) was added 2-chloroethanol (6.3 mL, 93.74 mmol) followed by a solution of BF$_3$ Et$_2$O (1.1 mL, 8.927 mmol) and DCE (20 mL). The pale yellow solution was stirred at 45° C. for 2 h. The reaction mixture was allowed to cool to RT, evaporated and dried in vacuo overnight (yield>95%) to afford 1-chloro-3-(2-chloro-ethoxy)-propan-2-ol.

step 2—The product from step 1 (16.06 g, 92.81 mmol) and 1M NaOH (185 mL, 185 mmol) were mixed and the biphasic mixture stirred at RT. After 2.5 h the reaction mixture was heated to 90° C. degrees for 2.5 h then allowed to cool to RT and evaporated. The remaining slurry was washed with DCM/MeOH (95:5) three times, filtered and the filtrate was evaporated. The remaining 9.5 g of oil was purified by SiO$_2$ chromatography (400 g SiO$_2$) eluting with a MeOH/DCM gradient (0-4% MeOH over 40 min) to afford a 30% yield of [1,4]dioxan-2-yl-methanol (114a).

step 3—To a solution of 114a (4.45 g, 37.67 mmol), TEA (6.3 mL, 45.2 mmol) and DCE cooled to 0° C. was added tosyl chloride (8.6 g, 45.2 mmol). The reaction mixture was allowed to warm to RT and stirred overnight. The reaction mixture was partitioned between with aqueous NH$_4$Cl. The aqueous layer was washed with DCM and the combined extracts dried (Na$_2$SO$_4$), filtered and evaporated. The residue was purified by SiO$_2$ chromatography eluting with an EtOAc/hexane gradient (0-30% EtOAc over 40 min) to afford a 95% yield of 114b.

Alkylation of A-9b with 114b, cleavage of the Boc protecting group and acylation of the resulting secondary amine with 4,6-dimethyl-pyrimidin-5-carboxylic acid was carried analogously to the procedures described in steps 2-4 of example 27.

H-10 was prepared analogously except in step 5,4,6-dimethyl-pyrimidin-5-carboxylic acid was replaced with 6-cyano-2,4-dimethyl nicotinic acid. II-11 and II-12 were prepared analogously starting from S-(+)-epichlorohydrin to prepare the dioxane moiety.

EXAMPLE 33

(S)-5-Butyl-9-[1-(4,6-dimethyl-pyrimidine-5-carbonyl)-4-methyl-piperidin-4-yl]-3-(6-fluoro-3-oxabicyclo[3.1.0]hex-6-ylmethyl)-1-oxa-3,9-diaza-spiro[5.5]undecan-2-one (II-13)

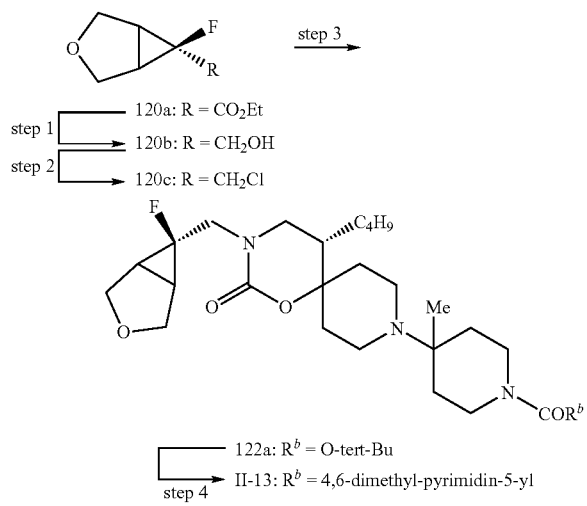

step 1—To a solution of 120a (0.086 g, 0.49 mmol) and THF (5 mL) cooled to −78° C. was added dropwise a solution of LiAlH$_4$ in THF (0.5 mL, 1.0 M solution in THF). The solution was stirred at −78° C. for 15 min, then allowed to warm to RT and stirred for 1 h. The reaction was quenched with Na$_2$SO$_4$.10H$_2$O (ca. 0.5 g) and the resulting mixture stirred for another hour. The resulting solution was filtered through a bed of CELITE which was washed with DCM and the organic solution was evaporated to afford 120b which was used in the next step without further purification.

step 2—To a solution of 120b from step 1 (ca. 0.49 mmol) dissolved in pyridine/DCM (2 mL, 1:1) was added tosyl chloride (0.0988 g, 0.51 mmol). After 2 addition aliquots of TsCl were added and stirring continued at RT for 72 h, starting material remained in the reaction solution. The solution was transferred to a microwave vial and an additional 0.099 g of TsCl added and the resulting solution heated at 150° C. for 1 h. The resulting solution was cooled and partitioned between DCM and 10% HCl. The aqueous acid was extracted with DCM and the combined DCM extracts washed with water, dried, filtered and evaporated to afford 120c which was used directly in step 3.

step 3—A reaction flask was charged with A-9b (R$^b$=tert-butoxy, 0.323 g, 0.74 mmol), 120c (ca. 0.49 mmol), NaOH (0.079 g, 1.97 mmol), NBu$_4$Br (0.008 g, 0.025 mmol) and toluene (3 mL) and the resulting mixture heated to 55° C. for 100 h, then stirred at RT for 170 h. The solution was partitioned between H$_2$O and DCM. The aqueous phase was extracted 4 times with DCM (50 mL each) and the combined extracts dried (MgSO$_4$), filtered and evaporated. The crude product was purified by SiO$_2$ chromatography eluting with a gradient of DCM and a solution of DCM/MeOH/NH$_4$OH (60/10/1) (100 to 30% DCM) to afford 0.19 g of 122a.

step 4—A solution of 122a (0.19 g) was dissolved in DCM/TFA (5 mL, 1:1) and stirred at RT for 18 h. The solvent was evaporated and the residue twice taken up in 10 mL of toluene and re-evaporated. The crude product was purified by SiO$_2$ chromatography eluting with a gradient of DCM and a solution of DCM/MeOH/NH$_4$OH (60/10/1) (100 to 20% DCM) to afford 0.060 g of the amine sufficiently pure to use in the subsequent acylation. A solution of the amine, 2,4-dimethyl-pyrimidine-5-carboxylic acid, EDCI (0.022 g, 0.1027 mmol), HOBt (0.014 g, 0.1027 mmol), DIPEA (0.048 mL, 0.274 mmol) and DCM (3 mL) was stirred at RT for 18 h. A second aliquot of all reagents were added and stirring continued for an additional 18 h. The solvents were evaporated and the residue purified by SiO$_2$ chromatography eluting with a gradient of DCM and a solution of DCM/MeOH/NH$_4$OH (60/10/1) (100 to 70% DCM). The recovered material was further chromatographed on a SiO$_2$ column eluting with a MeOH/DCM (0 to 10% MeOH) and dried in vacuo to afford II-13.

EXAMPLE 34

Human CCR5 Receptor-Ligand Binding Assay Protocol

Human CCR5 receptor (Genebank ID: 29169292) was cloned into mammalian expression vector, pTarget (Promega). The construct was transfected into CHO-G$_{\alpha16}$ cells by using Fugene Reagent (Roche). Clones were selected under antibiotic pressure (G418 and Hygromycin) and sorted 4 times with a fluorescence activates cell sorter and a monoclonal antibody specific for CCR5 receptor (BD Biosciences Pharmigen, Mab 2D7, Cat. No. 555993). The clone with highest expression (100,000 copies per cell) was chosen for the binding assays.

Adherent cells in 225 mL tissue culture flask (ca. 90% confluent) were harvested using 1 mM EDTA in PBS (phosphate-buffered saline) without Ca$^{2+}$ and Mg$^{2+}$. Cells were washed twice with PBS containing no Ca$^{2+}$ and Mg$^{2+}$. CHO-G$_{\alpha16}$-hCCR5 cells were then resuspended (1×10$^6$/mL) in ice cold binding buffer (50 mM HEPES, 1 mM CaCl$_2$, 5 mM MgCl$_2$, 0.5% BSA, 0.05% NaN$_3$, pH 7.24), pH 7.4), supplemented with freshly made 0.5% BSA and 0.05% NaN$_3$.

Eighty μl CHO-G$_{\alpha16}$-hCCR5 (1×10$^6$/mL) cells were added to 96 well plates. All dilutions were made in binding buffer (50 mM HEPES, 1 mM CaCl$_2$, 5 mM MgCl$_2$, 0.5% BSA, 0.05% NaN$_3$, pH 7.24).

The plates were incubated on a cell shaker at RT for 2 h with a final concentration of 0.11 nM 1251 RANTES or $^{125}$I MIP-1α or 1251 MIP-1β. The compound dilutions were made in PBS, 1% BSA. Total reaction volume was 100 μl per well. The test compounds were added to the cells prior to the addition of radioligand.

After incubation, the cells were harvested onto GF/C filter plates using Packard cell harvester. Filters were pretreated with 0.3% PEI/0.2% BSA for 30 min. The filter plate was washed rapidly 5 times with 25 mM HEPES, 500 mM NaCl, 1 mM CaCl$_2$ and 5 mM MgCl$_2$ adjusted to pH 7.1. Plates were dried in oven (70° C.) for 20 min, added with 40 µl scintillation fluid and sealed with Packard TopSeal-A. Packard Top Count was used to measure of the radioactivity for 1 min per well.

Total binding was determined with control wells added with radioisotope and buffer and the non-specific binding was determined using an excess cold RANTES to some of the control wells. Specific binding was determined by subtracting the non-specific form total binding. Results are expressed as the percentage of specific $^{125}$I RANTES binding. IC$_{50}$ values were determined using varying concentrations of the test ligand in triplicates and the data was analyzed using GraphPad Prism (GraphPad, San Diego, Calif.). Typical data are tabulated in TABLE V.

TABLE V

| Compound No. | IC$_{50}$ µM |
| --- | --- |
| I-2 | 0.0162 |
| II-4 | 0.0108 |
| II-6 | 0.038 |
| II-10 | 0.0172 |
| III-6 | 0.0465 |
| III-12 | 0.0494 |
| III-20 | 0.014 |
| III-22 | 0.0212 |
| III-23 | 0.0388 |
| IV-7 | 0.0192 |
| IV-13 | 0.0492 |

EXAMPLE 35

CCR5—Mediated CCF Assay

CCF assay was performed as described before (C. Ji, J. Zhang, N. Cammack and S. Sankuratri, *J. Biomol. Screen.* 2006 11(6):652-663). Hela-R5 cells (express gp160 from R5-tropic virus and HIV-1 Tat) were plated in 384 well white culture plates (BD Bioscience, Palo Alto, Calif.) at 7.5×1 cells per well in phenol red-free Dulbecco's Modified Eagle Medium (DMEM) supplemented with 10% FBS, 1× Pen-Strep, 300 µg/mL G418, 100 µg/mL hygromycin, and 1 µg/mL Doxycycline (Dox) (BD Bioscience, Palo Alto, Calif.), using Multimek (Beckman, Fullerton, Calif.) and incubated at 37° C. overnight to induce the expression of gp160. Ten µL diluted compounds in medium containing 5% DMSO were added to the cells, followed by the addition of CEM-NKr-CCR5-Luc (obtained from NIH AIDS Research & Reference Reagents Program) that expresses CD4 and CCR5 and carries a HIV-2 long terminal repeat (LTR)-driven luciferase reporter gene at 1.5×10$^4$ cells/15 µL/well and incubated for 24 hrs. At the end of co-culture, 15 µL of Steady-Glo luciferase substrate was added into each well, and the cultures were sealed and gently shaken for 45 min. The luciferase activity were measured for 10 sec per well as luminescence by using 16-channel TopCount NXT (PerkinElmer, Shelton, CT) with 10 min dark adaptation and the readout is count per second (CPS). For the drug interaction experiments, small molecule compounds or antibodies were serially diluted in serum-free and phenol red-free RPMI containing 5% DMSO (CalBiochem, La Jolla, Calif.) and 1× Pen-Strep. Five µL each of the two diluted compound or mAb is to be tested for drug-drug interactions were added to the Hela-R5 cells right before the addition of target cells. Typical data are tabulated in TABLE VI.

TABLE VI

| Cpd. No. | IC$_{50}$ (µM) |
| --- | --- |
| III-1 | 0.0252 |
| III-2 | 0.0174 |
| II-10 | 0.001 |
| III-22 | 0.003 |
| IV-13 | 0.02 |
| III-20 | <0.0025 |
| III-23 | <0.0025 |

EXAMPLE 36

HIV-1 Single Cycle Antiviral Assay

The sensitivity of a recombinant HIV-1 virus pseudotyped with the envelope proteins of the CCR5-tropic virus NLBal to test compounds was determined in a Luciferase reporter assay using JC53BL cells. NLBal pseudotyped HIV-1 was generated by calcium phosphate transfection of 293T cells (ATCC) with equal amounts of DNA of an envelope-deleted HIV-1 plasmid and of a NLBal envelope expression plasmid. The media (DMEM, 10% fetal bovine serum, 1% Penicillin/streptomycin, 1% Glutamine, all Gibco) was changed 16 h post-transfection and virus containing supernatant was harvested 48 h post-transfection. To determine the sensitivity of NLBal pseudotyped HIV-1, 25.000 JC53BL cells (NIH AIDS Reagent Program) were infected with NLBal pseudotyped HIV-1 in presence of a drug gradient in white 96 well plates (Greiner Bio-one). The volume was adjusted to 200 µL using assay media (DMEM, 10% fetal bovine serum, 1% Penicillin/streptomycin, 1% Glutamine). After incubation at 37° C., 90% relative humidity, 5% CO$_2$ for 3 days, 50 µL of Steady-Glo® Luciferase reagent (Promega) was added, incubated for 5 min at RT and luminescence was measured using a luminometer (Luminoskan, Thermo). The 50% and 90% inhibitory concentrations were calculated using Microsoft XL Fit 4 software. Typical data are tabulated in TABLE VII.

TABLE VII

| Cpd. No. | IC$_{50}$ (µM) |
| --- | --- |
| I-8 | 0.0052 |
| I-9 | 0.0025 |
| II-10 | 0.0026 |
| III-22 | 0.0022 |
| IV-13 | 0.084 |
| III-20 | 0.003 |
| III-23 | 0.006 |

EXAMPLE 37

Chemotaxis Assay

L1.2hCCR5 cells are cultured in RPMI 1640 containing 10% fetal bovine serum, 10 µg/mL penicillin/streptomycin, 0.1 mM glutamine, 1M sodium pyruvate, 55 µM β-mercaptoethanol, and 250 µg/mL geneticin (all from Invitrogen). Just prior to the set up of the chemotaxis assay, the cells are spun down and resuspended in Chemotaxis Buffer (Hank's Balanced Salt Solution HBSS (Invitrogen) containing 0.1% BSA and 10 mM HEPES). The cells are used in the chemotaxis assay at a final concentration of 5×10$^6$ cells/mL.

CCR5 ligands hMIP1α, hMIP1β or hRANTES (R&D Systems) are diluted in Chemotaxis Buffer and are used at a final concentration of 10 nM. Test substances and the appropriate vehicle control are diluted in Chemotaxis Buffer.

The chemotaxis assay is set up in the 0.5 μm pore 96-well ChemoTx$^R$ system (Neuroprobe). Each test or control substance is mixed with one of the CCR5 ligands and 30 μL of this mixture is placed in the bottom well of the ChemoTx$^R$ system. The filter screen in placed on top of the bottom wells and forms the top wells. Each test or control substance is mixed with the L1.2hCCR5 cells and 20 μL of this mixture is placed on the top wells. The plates are then placed in a humidified chamber and incubated at 37° C. and 5% $CO_2$ for 3 h.

After the incubation period, the cells are scraped off the filter and the plates are spun in a table top centrifuge at 2,000 rpm for 10 min. The filter is then removed and the density of the cells that have migrated to the bottom wells is detected using CyQUANT$^R$ cell proliferation assay kit (Invitrogen) and the Spectra MAX GeminiXS plate reader (Molecular Devices) according to the manufacturers' instructions. Using the fluorescence measurements the percent migration is determined by % migration=[1−(max−obs)/(max−min)]×100. The observed value (obs) is the value observed in the test well. The maximum (max) is the average of ligand+control and the minimum (min) is the average of the no ligand+control. The $IC_{50}$ is defined at the midpoint between the minimum and maximum of the dose response curve. This is calculated with Excel Fit. Data are tabulated in TABLE VIII.

TABLE VIII

| Cpd. No. | $IC_{50}$ (μM) |
|---|---|
| I-2 | 0.237 |
| I-5 | 0.023 |

1. Inhibition of RANTES stimulated chemotaxis

EXAMPLE 38

Pharmaceutical compositions of the subject Compounds for administration via several routes were prepared as described in this Example.

Composition for Oral Administration (A)

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

Parenteral Formulation (D)

| Ingredient | % wt./wt. |
|---|---|
| Active ingredient | 0.25 g |
| Sodium Chloride | qs to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations (G)

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound according to formula I wherein:

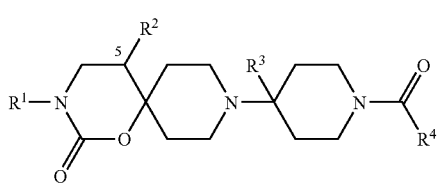
(I)

$R^1$ is:
(a) $C_{3-6}$ cycloalkyl,
wherein said cycloalkyl is optionally substituted with one to three groups independently selected from the group consisting of hydroxy, $C_{1-3}$ alkyl, oxo, halogen, $C_{1-6}$ alkoxy-oximino, and $C_{1-6}$ alkoxy-$C_{1-6}$ alkyloxy;
(b) $C_{3-6}$ cycloalkyl-$C_{1-3}$ alkyl
wherein said cycloalkyl is optionally substituted with one to three groups independently selected from the group consisting of hydroxy, $C_{1-3}$ alkyl, oxo, halogen, $C_{1-6}$ alkoxy-oximino and $C_{1-6}$ alkoxy-$C_{1-6}$ alkyloxy with the proviso that said $C_{3-6}$ cycloalkyl-$C_{1-3}$ alkyl is not 4,4-difluorocyclohexyl-methyl or 1-hydroxyl-cyclohexyl-methyl (c) 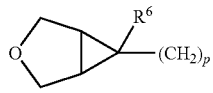

wherein $R^6$ is hydrogen or halogen;

(d) 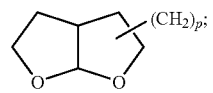

(e) 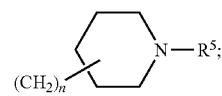

(f) 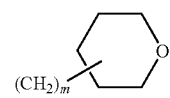

wherein m is 0 or 2;
(g) heteroaryl, heteroaryl $C_{1-3}$ alkyl, phenyl $C_{1-3}$ alkyl
wherein said heteroaryl is pyridine, pyrimidine, pyrazine or pyridazine and said heteroaryl or said phenyl is independently substituted with 1 to 3 substituents independently selected from $C_{1-6}$ alkyl, halogen, $C_{1-6}$ alkoxy, cyano or nitro;
(h) $C_{1-6}$ haloalkyl;

(i) 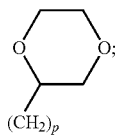

(j) 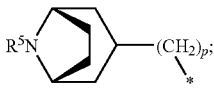

(k) 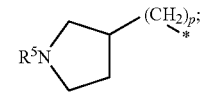

(I)

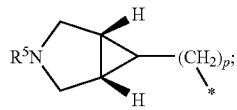

R² is C₁₋₆ alkyl;
R³ is hydrogen or C₁₋₃ alkyl;
R⁴ is selected from the group consisting of (a)-(k) and (l):
 (a) 4,6-dimethyl-pyrimidin-5-yl;
 (b) 4,6-dimethyl-2-trifluoromethyl-pyrimidin-5-yl;
 (c) 2,4-dimethyl-pyridin-3-yl;
 (d) 2,4-dimethyl-1-oxy-pyridin-3-yl
 (e) 6-cyano-2,4-dimethyl-pyridin-3-yl;
 (f) 2,4-dimethyl-6-oxo-6H-pyran-3-yl
 (g) 2,4-dimethyl-6-oxo-1,6-dihydro-pyridin-3-yl;
 (h) 1,2,4-trimethyl-6-oxo-1,6-dihydro-pyridin-3-yl;
 (i) 3,5-dimethyl-1-oxy-1H-pyrazol-4-yl;
 (j) 5-cyano-2,4-dimethyl-1H-pyrrol-3-yl;
 (k) 3-methyl-5-trifluoromethyl-isoxazol-4-yl; and,
 (l) 3,5-dimethyl-1-hydroxy-pyrazol-4-yl;
R⁵ is C₁₋₆ acyl, C₁₋₆ alkoxycarbonyl, C₁₋₆ alkyl SO₂, C₁₋₆ haloalkyl, C₃₋₆ cycloalkyl, oxetanyl, tetrahydrofuranyl or tetrahydropyranyl;
n is 0 to 3; and,
p is 1 or 3; or,
a pharmaceutically acceptable acid addition salt thereof.

2. A compound according to claim 1 wherein R¹ is 4-alkoxy-cyclohexylmethyl, or 4-hydroxy-cyclohexylmethyl, R³ is methyl and R⁴ is (a), (c) or (e).

3. A compound according to claim 2 wherein the C-5 configuration is S.

4. A compound according to claim 1 wherein R¹ is (e), (j), (k) or (l), R³ is methyl and R⁴ is (a), (c) or (e).

5. A compound according to claim 4 wherein R⁵ is C₁₋₆ alkoxycarbonyl or 2,2-difluoroethyl.

6. A compound according to claim 5 wherein the C-5 configuration R² is S.

7. A compound according to claim 1 wherein R¹ is (c), (d) or (i), R³ is methyl and R⁴ is (a), (c) or (e).

8. A compound according to claim 1 wherein R¹ is (g), R³ is methyl, R⁴ is (a), (c) or (e) and the C-5 configuration is S.

9. A compound according to claim 1 which compound is selected from the group consisting of:
 5-butyl-9-[1-(4,6-dimethyl-pyrimidine-5-carbonyl)-4-methyl-piperidin-4-yl]-3-((1S,3S)-3-methoxy-cyclohexylmethyl)-1-oxa-3,9-diaza-spiro[5.5]undecan-2-one,
 (S)-5-butyl-9-[1-(4,6-dimethyl-pyrimidine-5-carbonyl)-4-methyl-piperidin-4-yl]-3-(4-methoxy-cyclohexylmethyl)-1-oxa-3,9-diaza-spiro[5.5]undecan-2-one,
 (S)-5-butyl-9-[1-(4,6-dimethyl-pyrimidine-5-carbonyl)-4-methyl-piperidin-4-yl]-3-(4-methoxy-cyclohexylmethyl)-1-oxa-3,9-diaza-spiro[5.5]undecan-2-one,
 (S)-5-butyl-9-[1-(4,6-dimethyl-piperidine-5-carbonyl)-4-methyl-piperidin-4-yl]-3-(4-hydroxy-cyclohexylmethyl)-1-oxa-3,9-diaza-spiro[5.5]undecan-2-one,
 (S)-5-butyl-9-[1-(4,6-dimethyl-pyrimidine-5-carbonyl)-4-methyl-piperidin-4-yl]-3-(4-hydroxy-cyclohexylmethyl)-1-oxa-3,9-diaza-spiro[5.5]undecan-2-one,
 (S)-5-butyl-9-[1-(4,6-dimethyl-pyrimidine-5-carbonyl)-4-methyl-piperidin-4-yl]-3-(4-ethoxy-cyclohexylmethyl)-1-oxa-3,9-diaza-spiro[5.5]undecan-2-one,
 (S)-5-butyl-9-[1-(4,6-dimethyl-pyrimidine-5-carbonyl)-4-methyl-piperidin-4-yl]-3-(4-ethoxy-cyclohexylmethyl)-1-oxa-3,9-diaza-spiro[5.5]undecan-2-one,
 (S)-5-butyl-9-[1-(4,6-dimethyl-pyrimidine-5-carbonyl)-4-methyl-piperidin-4-yl]-3-(4-methoxymethoxy-cyclohexylmethyl)-1-oxa-3,9-diaza-spiro[5.5]undecan-2-one,
 (S)-5-butyl-9-[1-(4,6-dimethyl-pyrimidine-5-carbonyl)-4-methyl-piperidin-4-yl]-3-(4-methoxymethoxy-cyclohexylmethyl)-1-oxa-3,9-diaza-spiro[5.5]undecan-2-one,
 5-{4-[(S)-5-butyl-3-(4-hydroxy-cyclohexylmethyl)-2-oxo-1-oxa-3,9-diaza-spiro[5.5]undec-9-yl]-4-methyl-piperidine-1-carbonyl}-4,6-dimethyl-pyridine-2-carbonitrile,
 (S)-5-butyl-9-[1-(4,6-dimethyl-pyrimidine-5-carbonyl)-4-methyl-piperidin-4-yl]-3-[(1R,5S,6S)-1-(3-oxa-bicyclo[3.1.0]hex-6-yl)methyl]-1-oxa-3,9-diaza-spiro[5.5]undecan-2-one,
 5-(4-{(S)-5-butyl-3-[(1R,5S,6S)-1-(3-oxa-bicyclo[3.1.0]hex-6-yl)methyl]-2-oxo-1-oxa-3,9-diaza-spiro[5.5]undec-9-yl}-4-methyl-piperidine-1-carbonyl)-4,6-dimethyl-pyridine-2-carbonitrile,
 (S)-5-butyl-9-[1-(4,6-dimethyl-2-trifluoromethyl-pyrimidine-5-carbonyl)-4-methyl-piperidin-4-yl]-3-[(1R,5S,6S)-1-(3-oxa-bicyclo[3.1.0]hex-6-yl)methyl]-1-oxa-3,9-diaza-spiro[5.5]undecan-2-one,
 (S)-5-butyl-9-[1-(6-difluoromethyl-2,4-dimethyl-pyridine-3-carbonyl)-4-methyl-piperidin-4-yl]-3-(3-oxa-bicyclo[3.1.0]hex-6-ylmethyl)-1-oxa-3,9-diaza-spiro[5.5]undecan-2-one,
 (S)-5-butyl-9-[1-(4,6-dimethyl-pyrimidine-5-carbonyl)-4-methyl-piperidin-4-yl]-3-(hexahydro-furo[2,3-b]furan-3-ylmethyl)-1-oxa-3,9-diaza-spiro[5.5]undecan-2-one,
 (S)-5-butyl-9-[1-(4,6-dimethyl-pyrimidine-5-carbonyl)-4-methyl-piperidin-4-yl]-3-(hexahydro-furo[2,3-b]furan-3-ylmethyl)-1-oxa-3,9-diaza-spiro[5.5]undecan-2-one,
 5-{4-[(S)-5-butyl-3-(hexahydro-furo[2,3-b]furan-3-ylmethyl)-2-oxo-1-oxa-3,9-diaza-spiro[5.5]undec-9-yl]-4-methyl-piperidine-1-carbonyl}-4,6-dimethyl-pyridine-2-carbonitrile,
 5-butyl-9-[1-(2,4-dimethyl-pyridine-3-carbonyl)-4-methyl-piperidin-4-yl]-3-(hexahydro-furo[2,3-b]furan-3-ylmethyl)-1-oxa-3,9-diaza-spiro[5.5]undecan-2-one;
 (S)-5-butyl-9-[1-(4,6-dimethyl-pyrimidine-5-carbonyl)-4-methyl-piperidin-4-yl]-3-(R)-1-[1,4]dioxan-2-ylmethyl-1-oxa-3,9-diaza-spiro[5.5]undecan-2-one,
 5-[4-((S)-5-butyl-3-(R)-1-[1,4]dioxan-2-ylmethyl-2-oxo-1-oxa-3,9-diaza-spiro[5.5]undec-9-yl)-4-methyl-piperidine-1-carbonyl]-4,6-dimethyl-pyridine-2-carbonitrile,
 (S)-5-butyl-9-[1-(4,6-dimethyl-pyrimidine-5-carbonyl)-4-methyl-piperidin-4-yl]-3-(S)-1-[1,4]dioxan-2-ylmethyl-1-oxa-3,9-diaza-spiro[5.5]undecan-2-one,
 5-[4-((S)-5-butyl-3-(S)-1-[1,4]dioxan-2-ylmethyl-2-oxo-1-oxa-3,9-diaza-spiro[5.5]undec-9-yl)-4-methyl-piperidine-1-carbonyl]-4,6-dimethyl-pyridine-2-carbonitrile,
 (S)-5-butyl-9-[1-(4,6-dimethyl-pyrimidine-5-carbonyl)-4-methyl-piperidin-4-yl]-3-((1S,5R,6R)-6-fluoro-3-oxa-bicyclo[3.1.0]hex-6-ylmethyl)-1-oxa-3,9-diaza-spiro[5.5]undecan-2-one,
 3-(1-acetyl-piperidin-4-ylmethyl)-5-butyl-9-[1-(4,6-dimethyl-pyrimidine-5-carbonyl)-4-methyl-piperidin-4-yl]-1-oxa-3,9-diaza-spiro[5.5]undecan-2-one, 3-(1-acetyl-piperidin-3-ylmethyl)-5-butyl-9-[1-(4,6-dimethyl-pyrimidine-5-carbonyl)-4-methyl-piperidin-4-yl]-1-oxa-3,9-diaza-spiro[5.5]undecan-2-one, 5-butyl-9-[1-(4,6-dimethyl-pyrimidine-5-carbonyl)-4-methyl-piperidin-4-yl]-3-(1-isobutyryl-piperidin-4-ylmethyl)-1-oxa-3,9-diaza-spiro[5.5]undecan-2-one, 3-[2-(1-acetyl-piperidin-4-yl)-ethyl]-5-butyl-9-[1-(4,6-dimethyl-pyrimidine-5-carbonyl)-4-methyl-piperidin-4-yl]-1-oxa-3,9-diaza-spiro[5.5]undecan-2-one, 5-butyl-9-[1-(4,6-dimethyl-pyrimidine-5-carbonyl)-4-methyl-piperidin-4-yl]-3-(1-methanesulfonyl-piperidin-4-ylmethyl)-1-oxa-3,9-diaza-spiro[5.5]undecan-2-one, 4-{(S)-5-butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-piperidine-1-carboxylic acid methyl ester, 3-{5-butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-piperidine-1-carboxylic acid methyl ester, 4-{(S)-5-butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-piperidine-1-carboxylic acid ethyl ester, (S)-5-butyl-9-[1-(4,6-dimethyl-pyrimidine-5-carbonyl)-4-methyl-piperidin-4-yl]-3-(1-oxetan-3-yl-piperidin-4-ylmethyl)-1-oxa-3,9-diaza-spiro[5.5]undecan-2-one, (S)-5-butyl-3-(1-cyclopropyl-piperidin-4-ylmethyl)-9-[1-(4,6-dimethyl-pyrimidine-5-carbonyl)-4-methyl-piperidin-4-yl]-1-oxa-3,9-diaza-spiro[5.5]undecan-2-one, (S)-5-butyl-3-[1-(2,2-difluoro-ethyl)-piperidin-4-ylmethyl]-9-[1-(4,6-dimethyl-pyrimidine-5-carbonyl)-4-methyl-piperidin-4-yl]-1-oxa-3,9-diaza-spiro[5.5]undecan-2-one, 5-(4-{(S)-5-butyl-3-[1-(2,2-difluoro-ethyl)-piperidin-4-ylmethyl]-2-oxo-1-oxa-3,9-diaza-spiro[5.5]undec-9-yl}-4-methyl-piperidine-1-carbonyl)-4,6-dimethyl-pyridine-2-carbonitrile, (S)-3-{(S)-5-butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-pyrrolidine-1-carboxylic acid ethyl ester, (S)-3-{(S)-5-butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-pyrrolidine-1-carboxylic acid methyl ester, (S)-5-butyl-3-[(S)-1-(2,2-difluoro-ethyl)-pyrrolidin-3-ylmethyl]-9-[1-(4,6-dimethyl-pyrimidine-5-carbonyl)-4-methyl-piperidin-4-yl]-1-oxa-3,9-diaza-spiro[5.5]undecan-2-one, (R)-3-{(S)-5-butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-pyrrolidine-1-carboxylic acid methyl ester, (1R,5S,6R)-6-{(S)-5-butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-3-aza-bicyclo[3.1.0]hexane-3-carboxylic acid ethyl ester, (S)-5-butyl-3-[(1R,5S,6R)-3-(2,2-difluoro-ethyl)-3-aza-bicyclo[3.1.0]hex-6-ylmethyl]-9-[1-(4,6-dimethyl-pyrimidine-5-carbonyl)-4-methyl-piperidin-4-yl]-1-oxa-3,9-diaza-spiro[5.5]undecan-2-one, (S)-5-butyl-3-[(1R,5S,6R)-3-(2,2-difluoro-ethyl)-3-aza-bicyclo[3.1.0]hex-6-ylmethyl]-9-[1-(4,6-dimethyl-pyrimidine-5-carbonyl)-4-methyl-piperidin-4-yl]-1-oxa-3,9-diaza-spiro[5.5]undecan-2-one, (1R,5S,6R)-6-{(S)-5-butyl-9-[4-methyl-1-(3-methyl-5-trifluoromethyl-isoxazole-4-carbonyl)-piperidin-4-yl]-2-oxo-1-oxa-3,9-diaza-spiro[5.5]undec-3-ylmethyl}-3-aza-bicyclo[3.1.0]hexane-3-carboxylic acid methyl ester, (S)-3-((1R,5S,6R)-3-acetyl-3-aza-bicyclo[3.1.0]hex-6-ylmethyl)-5-butyl-9-[4-methyl-1-(3-methyl-5-trifluoromethyl-isoxazole-4-carbonyl)-piperidin-4-yl]-1-oxa-3,9-diaza-spiro[5.5]undecan-2-one, (1S,3R,5R)-3-{(S)-5-butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-8-aza-bicyclo[3.2.1]octane-8-carboxylic acid methyl ester, (S)-5-butyl-3-(1-methanesulfonyl-piperidin-4-ylmethyl)-9-[4-methyl-1-(3-methyl-5-trifluoromethyl-isoxazole-4-carbonyl)-piperidin-4-yl]-1-oxa-3,9-diaza-spiro[5.5]undecan-2-one, 4-{(S)-5-butyl-9-[4-methyl-1-(3-methyl-5-trifluoromethyl-isoxazole-4-carbonyl)-piperidin-4-yl]-2-oxo-1-oxa-3,9-diaza-spiro[5.5]undec-3-ylmethyl}-piperidine-1-carboxylic acid methyl ester, (S)-3-(1-acetyl-piperidin-4-ylmethyl)-5-butyl-9-[4-methyl-1-(3-methyl-5-trifluoromethyl-isoxazole-4-carbonyl)-piperidin-4-yl]-1-oxa-3,9-diaza-spiro[5.5]undecan-2-one;

(S)-3-(1-acetyl-piperidin-3-ylmethyl)-5-butyl-9-[4-methyl-1-(3-methyl-5-trifluoromethyl-isoxazole-4-carbonyl)-piperidin-4-yl]-1-oxa-3,9-diaza-spiro[5.5]undecan-2-one; compound with formic acid, 5-butyl-3-(3,3-difluoro-cyclobutylmethyl)-9-[1-(4,6-dimethyl-pyrimidine-5-carbonyl)-4-methyl-piperidin-4-yl]-1-oxa-3,9-diaza-spiro[5.5]undecan-2-one, (S)-5-butyl-9-[1-(4,6-dimethyl-pyrimidine-5-carbonyl)-4-methyl-piperidin-4-yl]-3-(4-oxo-cyclohexylmethyl)-1-oxa-3,9-diaza-spiro[5.5]undecan-2-one, 4-{5-butyl-9-[1-(4,6-dimethyl-pyrimidine-5-carbonyl)-4-methyl-piperidin-4-yl]-2-oxo-1-oxa-3,9-diaza-spiro[5.5]undec-3-ylmethyl}-benzonitrile, (S)-5-butyl-9-[1-(4,6-dimethyl-pyrimidine-5-carbonyl)-4-methyl-piperidin-4-yl]-3-(4-hydroxy-4-methyl-cyclohexylmethyl)-1-oxa-3,9-diaza-spiro[5.5]undecan-2-one, (S)-5-butyl-9-[1-(2,4-dimethyl-pyridine-3-carbonyl)-4-methyl-piperidin-4-yl]-3-pyrimidin-2-ylmethyl-1-oxa-3,9-diaza-spiro[5.5]undecan-2-one, 5-{4-[(S)-5-butyl-3-(4,6-dimethyl-pyrimidin-5-ylmethyl)-2-oxo-1-oxa-3,9-diaza-spiro[5.5]undec-9-yl]-4-methyl-piperidine-1-carbonyl}-4,6-dimethyl-pyridine-2-carbonitrile, (S)-5-butyl-3-(4,4-difluoro-cyclohexyl)-9-[1-(4,6-dimethyl-pyrimidine-5-carbonyl)-4-methyl-piperidin-4-yl]-1-oxa-3,9-diaza-spiro[5.5]undecan-2-one, (S)-5-butyl-9-[1-(4,6-dimethyl-piperidine-5-carbonyl)-4-methyl-piperidin-4-yl]-3-pyridin-2-yl-1-oxa-3,9-diaza-spiro[5.5]undecan-2-one, 5-[4-((S)-5-butyl-2-oxo-3-pyridin-2-yl-1-oxa-3,9-diaza-spiro[5.5]undec-9-yl)-4-methyl-piperidine-1-carbonyl]-4,6-dimethyl-pyridine-2-carbonitrile, (S)-5-butyl-9-[1-(4,6-dimethyl-pyrimidine-5-carbonyl)-4-methyl-piperidin-4-yl]-3-[2-(tetrahydro-pyran-4-yl)-ethyl]-1-oxa-3,9-diaza-spiro[5.5]undecan-2-one, (S)-5-butyl-9-[1-(4,6-dimethyl-pyrimidine-5-carbonyl)-4-methyl-piperidin-4-yl]-3-(4-methoxyimino-cyclohexylmethyl)-1-oxa-3,9-diaza-spiro[5.5]undecan-2-one, (S)-5-butyl-9-[1-(4,6-dimethyl-pyrimidine-5-carbonyl)-4-methyl-piperidin-4-yl]-3-(4-ethoxyimino-cyclohexylmethyl)-1-oxa-3,9-diaza-spiro[5.5]undecan-2-one, (S)-5-butyl-9-[1-(4,6-dimethyl-pyrimidine-5-carbonyl)-4-methyl-piperidin-4-yl]-3-(tetrahydro-pyran-4-yl)-1-oxa-3,9-diaza-spiro[5.5]undecan-2-one, and, 5-{4-[(S)-5-butyl-3-(2,2-difluoro-ethyl)-2-oxo-1-oxa-3,9-diaza-spiro[5.5]undec-9-yl]-4-methyl-piperidine-1-carbonyl}-4,6-dimethyl-pyridine-2-carbonitrile, and pharmaceutically acceptable salts thereof.

10. A method for treating a human immunodeficiency virus (HIV) infection in a patient in need thereof which comprises administering to the patient in need thereof a therapeutically effective amount of a compound according to claim 1.

11. A method according to claim 10 wherein $R^1$ is cis- or trans-4-alkoxy-cyclohexylmethyl or cis- or trans-4-hydroxy-cyclohexylmethyl, $R^3$ is methyl, $R^4$ is (a), (c) or (e) and the C-5 configuration is S.

12. A method according to claim 10 wherein $R^1$ is (e), (j), (k) or (l), $R^3$ is methyl, $R^4$ is (a), (c) or (e), $R^5$ is $C_{1-6}$ alkoxycarbonyl or 2,2,-difluoroethyl, n is 1 and the C-5 configuration is S.

13. A method according to claim 10 wherein $R^1$ is (c), (d) or (i), p is 1, $R^3$ is methyl, $R^4$ is (a), (c) or (e) and the C-5 configuration is S.

14. A method according to claim 10 further comprising co-administering a therapeutically effective amount of one or more inhibitors selected from the group consisting of HIV-1 nucleoside reverse transcriptase inhibitors, non-nucleoside reverse transcriptase inhibitors, HIV-1 protease inhibitors and HIV-1 viral fusion inhibitors and a compound of claim 1.

15. A method for treating rheumatoid arthritis comprising administering a therapeutically effective amount of a compound of according to claim 1 to a patient in need thereof.

16. A method according to claim 15 further comprising co-administering a therapeutically effective amount of one or more anti-inflammatory or analgesic compounds and a compound of claim 1 to a patient in need.

17. A method for treating asthma or congestive obstructive pulmonary disease (COPD) comprising administering a therapeutically effective amount of a compound according to claim 1 to a patient in need thereof.

18. A method for treating solid organ transplant rejection comprising administering a therapeutically effective amount of a compound according to claim 1 to a patient in need thereof.

19. A method according to claim 18 further comprising co-administering a therapeutically effective amount of one or more anti-rejection drugs or immunomodulators and a compound of claim 1 to a patient in need thereof.

20. A pharmaceutical composition comprising a compound according to claim 1 and at least one pharmaceutically acceptable carrier, diluent or excipient.

* * * * *